United States Patent
Arkenberg et al.

(10) Patent No.: US 11,761,923 B2
(45) Date of Patent: Sep. 19, 2023

(54) AMPEROMETRIC ELECTROCHEMICAL SENSORS, SENSOR SYSTEMS AND DETECTION METHODS

(71) Applicant: NEXCERIS INNOVATION HOLDINGS, LLC, Lewis Center, OH (US)

(72) Inventors: Gene B. Arkenberg, Columbus, OH (US); Scott L. Swartz, Columbus, OH (US); Matthew M. Seabaugh, Columbus, OH (US)

(73) Assignee: NEXTECH MATERIALS, LTD., Lewis Center, OH (US)

( * ) Notice: Subject to any disclaimer, the term of this patent is extended or adjusted under 35 U.S.C. 154(b) by 632 days.

(21) Appl. No.: 16/085,900

(22) PCT Filed: Mar. 17, 2017

(86) PCT No.: PCT/US2017/023069
§ 371 (c)(1),
(2) Date: Sep. 17, 2018

(87) PCT Pub. No.: WO2017/161335
PCT Pub. Date: Sep. 21, 2017

(65) Prior Publication Data
US 2019/0033248 A1    Jan. 31, 2019

Related U.S. Application Data

(63) Continuation-in-part of application No. 14/854,016, filed on Sep. 14, 2015, now abandoned.
(Continued)

(51) Int. Cl.
*G01N 27/407* (2006.01)
*F01N 11/00* (2006.01)
(Continued)

(52) U.S. Cl.
CPC ....... *G01N 27/4071* (2013.01); *F01N 11/002* (2013.01); *G01N 27/4067* (2013.01);
(Continued)

(58) Field of Classification Search
CPC ........... G01N 27/4071; G01N 27/4067; G01N 27/4076; G01N 27/416; G01N 33/0054;
(Continued)

(56) References Cited

U.S. PATENT DOCUMENTS 4,264,425 A * 4/1981 Kimura ................ G01N 27/417
                                                                                  204/412
5,190,834 A * 3/1993 Kendall ............... G01N 27/4073
                                                                                  429/466
(Continued)

FOREIGN PATENT DOCUMENTS

WO    WO-2009049091 A2 * 4/2009 ........... G01N 27/417

OTHER PUBLICATIONS

Diao et al. (Q Diao, F Yang, C Yin, J Li, S Yang, X Liang, G Lu, Ammonia sensors based on stabilized zirconia and CoWO4 sensing electrode, Solid State Ionics 225 (2012) 328-331) (Year: 2012).*
(Continued)

*Primary Examiner* — Joshua L Allen
(74) *Attorney, Agent, or Firm* — Porter Wright Morris & Arthur LLP

(57) ABSTRACT

An amperometric electrochemical sensor for measuring the concentrations of one or more target gas species in a gas sample or gas stream, the sensor having at least one electrochemical cell with first and second surface electrodes, an electrolyte layer and a passive signal amplifying layer ("SAL") comprising electrically conductive material like platinum, wherein at least a portion of the electrolyte layer is located between the surface electrodes and the SAL such that the SAL is in direct, conductive contact with the
(Continued)

electrolyte layer but is not in direct contact with the surface electrodes. Sensor systems and detection methods are also provided.

24 Claims, 17 Drawing Sheets

Related U.S. Application Data

(60) Provisional application No. 62/309,948, filed on Mar. 17, 2016, provisional application No. 62/049,977, filed on Sep. 12, 2014.

(51) Int. Cl.
 *G01N 27/406* (2006.01)
 *G01N 27/416* (2006.01)
 *G01N 33/00* (2006.01)

(52) U.S. Cl.
 CPC ..... *G01N 27/4076* (2013.01); *G01N 27/4162* (2013.01); *F01N 2560/026* (2013.01); *G01N 33/0054* (2013.01)

(58) Field of Classification Search
 CPC ........ G01N 27/406–41; G01N 33/0004–0075; F01N 11/002; F01N 2560/026; Y02A 50/20
 See application file for complete search history.

(56) References Cited

U.S. PATENT DOCUMENTS

| | | | | |
|---|---|---|---|---|
| 2005/0145493 | A1* | 7/2005 | Saffell | G01N 33/004 204/431 |
| 2008/0006532 | A1* | 1/2008 | Mukundan | G01N 27/4073 204/424 |
| 2009/0020422 | A1* | 1/2009 | A | G01N 33/0037 204/406 |
| 2009/0218220 | A1* | 9/2009 | Matter | G01N 27/4075 204/424 |
| 2010/0032292 | A1* | 2/2010 | Wang | G01N 33/0054 204/431 |
| 2012/0055789 | A1* | 3/2012 | Swartz | G01N 33/0037 204/415 |

OTHER PUBLICATIONS

Akiyama et al. (M. Akiyama, Z. Zhang, J. Tamaki, N. Miura, N. Yamazoe, T. Harada, Tunsten oxide-based semiconductor sensor for detection of nitrogen oxides in combustion exhaust, Sensors and Actuators B, 13-14 (1993) 619-620) (Year: 1993).*

Tamaki et al. (J. Tamaki, T. Fujii, K. Fujimoi, N. Miura, N. Yamazoe, Applications of metal tungstate-carbonate composite to nitrogen oxide sensor operative at elevated temperature, Sensors and Actuators B, 24-25 (1995) 396-399) (Year: 1995).*

* cited by examiner

Example 2:

525 °C, 200 mV Bias

- Baseline Signal: 3.8 µA
- 29% Sensitivity to 100 ppm NO
- 37% Sensitivity to 100 ppm $NO_2$
- 21% Sensitivity to 100 ppm $NH_3$ Example 1:

525 °C, 200 mV Bias

- Baseline Signal: 0.28 µA
- 2.5% Sensitivity to 100 ppm NO
- 2.1% Sensitivity to 100 ppm $NO_2$
- 8.9% Sensitivity to 100 ppm $NH_3$ Example 11:

Example 12:

AMPEROMETRIC ELECTROCHEMICAL SENSORS, SENSOR SYSTEMS AND DETECTION METHODS

CROSS REFERENCE TO RELATED APPLICATIONS

This application claims priority to U.S. Provisional Patent Application No. 62/309,948, filed on Mar. 17, 2016, entitled "Amperometric Electrochemical Sensors, Sensor Systems and Detection Methods." This application is a continuation-in-part of U.S. patent application Ser. No. 14/854,016, filed Sep. 14, 2015 (currently pending), which claims priority to U.S. Provisional Patent App. No. 62/049,977, filed Sep. 12, 2014, both of which are entitled "Amperometric Electrochemical Sensors, Sensor Systems and Detection Methods." The entire disclosures of the foregoing provisional and non-provisional patent applications are incorporated by reference herein.

STATEMENT REGARDING FEDERALLY SPONSORED RESEARCH OR DEVELOPMENT

The present invention was partially made with Government support under contract DE-SC-0009258 awarded by the United States Department of Energy. The Government has certain rights in the invention.

BACKGROUND

The increase in worldwide industrialization has generated concern regarding pollution created by combustion processes. Particularly, emissions from vehicles or other distributed sources are of concern. New environmental regulations are driving $NO_X$ (a mixture of NO and $NO_2$ of varying ratio) emissions from diesel fueled vehicles to increasingly lower levels, with the most challenging of these being the 2010 EPA Tier 2 diesel tailpipe standards.

To meet these emission regulations, engine manufacturers have been developing new diesel after-treatment technologies, such as selective catalyst reduction (SCR) systems and lean $NO_X$ traps (LNT). These technologies often require multiple $NO_X$ sensors to monitor performance and satisfy on-board diagnostics requirements for tailpipe emissions. Point of generation abatement technologies also have been developed for $NO_X$ along with other pollutants, but these solutions can reduce fuel efficiency if they are applied without closed loop control. Further, some of the proposed solutions themselves can be polluting if improperly controlled (e.g., selective catalytic reduction systems for $NO_X$ can release ammonia into the atmosphere). Control of these abatement technologies requires compact, sensitive sensors for $NO_X$, $NH_3$ and other pollutants that are capable of operating in oxygen-containing exhaust streams such as exhaust streams resulting from lean-burn engine operating conditions.

A number of approaches have been described for measuring the concentrations of $NO_X$ and $NH_3$. These include electrochemical, potentiometric (including mixed-potential), chemi-resistive, amperometric and impedance based methods. A good discussion of these approaches is provided in U.S. Pat. Nos. 8,974,657 and 9,304,102, which are incorporated by reference herein. In mixed-potential (potentiometric) sensors, for example, an EMF signal (an open circuit differential voltage) is generated in response to the presence of a target gas species due to non-equilibrium potentials between the sensing electrode and a reference electrode. No bias is applied between the sensing and reference electrodes of a mixed-potential sensor, and no ions (or electronic current) flow through the cell. Amperometric sensors, on the other hand, measure the current resulting from a voltage bias applied between the electrodes of an electrochemical cell.

Amperometric devices disclosed in the literature typically rely upon the catalytic decomposition of NOx to provide the detected current under the imposed voltage, as shown by the following equations:

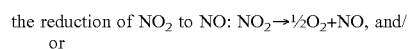

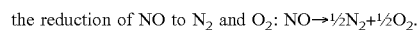

Other amperometric sensors such as those described in U.S. Pat. No. 9,304,102 are based on an adsorbed gas species (e.g., NOx) increasing the rate of oxygen reduction at the sensing electrode, rather than relying on the decomposition of that gas species (e.g., the catalytic decomposition of NOx) in order to sense target gas (e.g., NOx) concentration. An increase in oxygen reduction current, caused by the presence of adsorbed NOx, is used to detect the presence and/or concentration of NOx in oxygen-containing gas streams.

While a variety of devices and techniques may exist for accurately detecting $NO_X$, $NH_3$ and/or other target gas species, it is believed that no one prior to the inventors has made or used an invention as described herein.

BRIEF DESCRIPTION OF THE DRAWINGS

While the specification concludes with claims particularly pointing out and distinctly claiming the invention, it is believed that the invention will be better understood from the detailed description of certain embodiments thereof when read in conjunction with the accompanying drawings. Unless the context indicates otherwise, like numerals are used in the drawings to identify similar elements in the drawings. In addition, some of the figures may have been simplified by the omission of certain elements in order to more clearly show other elements. Such omissions are not necessarily indicative of the presence or absence of particular elements in any of the exemplary embodiments, except as may be explicitly stated in the corresponding detailed description.

Figure 1:
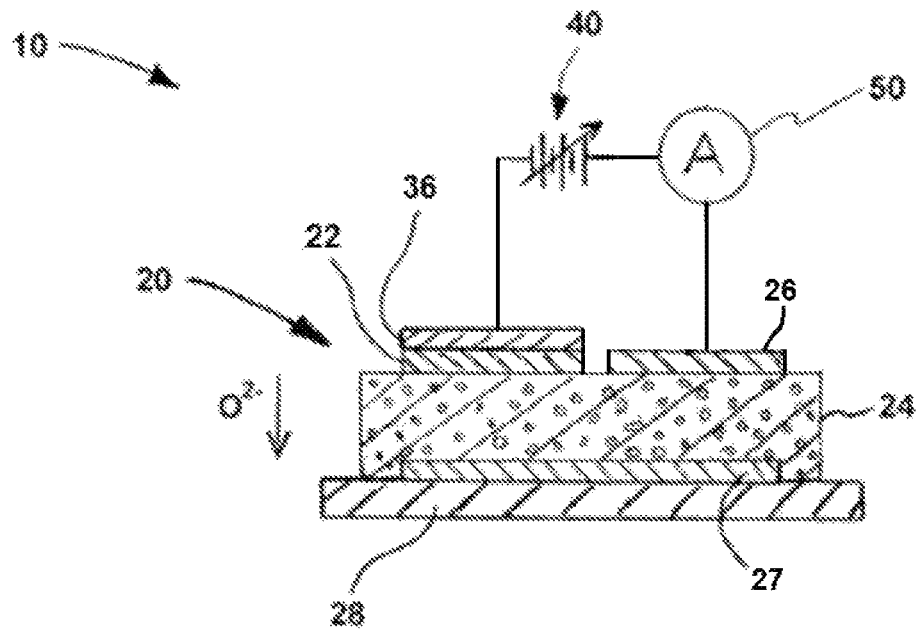
FIG. 1 is a schematic, cross-sectional view of an electrochemical sensor incorporated into a sensor system, wherein the active and counter electrodes are located on the same side of the electrolyte layer (i.e., surface electrodes), the active electrode has a full coverage current collector layer, and a passive, signal amplifying layer is located on the opposite side of the electrolyte layer, encapsulated (i.e., buried) between the electrolyte layer and the supporting substrate.

The drawings are intended to illustrate rather than limit the scope of the present invention. Embodiments of the present invention may be carried out in ways not necessarily depicted in the drawings. Thus, the drawings are intended to merely aid in the explanation of the invention. Thus, the present invention is not limited to the precise arrangements shown in the drawings.

DETAILED DESCRIPTION

The following detailed description describes examples of embodiments of the invention solely for the purpose of enabling one of ordinary skill in the relevant art to make and use the invention. As such, the detailed description and illustration of these embodiments are purely illustrative in nature and are in no way intended to limit the scope of the invention, or its protection, in any manner. It should also be understood that the drawings are not to scale and in certain instances details have been omitted, which are not necessary for an understanding of the present invention.

The present disclosure provides amperometric electrochemical sensors, as well as sensor systems and gas species detection methods employing such sensors, wherein those sensors comprise two (or more) surface electrodes located on an electrolyte, as well as a passive, conductive, signal amplifying layer. The signal amplifying layer is positioned in contact with the electrolyte and below, but not in contact with, the surface electrodes (e.g., encapsulated within or immediately below the electrolyte layer). The signal amplifying layer, despite being spaced away from the surface electrodes by the electrolyte layer, enhances signal strength and, in some instances, desirably affects sensor selectivity with respect to one or more gas species. In one study further discussed herein, the addition of a signal amplifying layer between the bottom surface of the electrolyte layer and the sensor substrate increased the signal strength of the sensor more than tenfold while also significantly increasing the sensor's sensitivity to NO, $NO_X$ and $NH_3$. While not wanting to be bound by theory, it is believed that the signal amplifying layer provides a lateral current path and effectively increases the areas of the active and counter electrodes. This finding is surprising in that electricity is normally conducted between the electrodes through or along the surface of the electrolyte layer by oxygen ions only. It is believed that when the signal amplifying layer is present, some of the oxygen ions, normally conducted between the electrodes through the electrolyte layer, are converted into electrons at the interface of the electrolyte layer and the signal amplifying layer. These electrons are then transported through the signal amplifying layer and thereafter react with oxygen to form oxygen ions at the interface of the signal amplifying layer and the electrolyte layer. Even though this requires two additional electrochemical reactions, the signal amplifying layer provides a faster pathway for the transport of charge carriers between the electrodes. While this finding can be applied to a variety of amperometric sensors having surface electrodes (including interdigitated electrodes), it is particularly useful for other types of sensors wherein electrode layers are deposited onto materials with much lower conductivity than the material used for the signal amplifying layers. The signal amplifying layer also allows for larger spacing between the surface electrodes, which can simplify sensor fabrication.

U.S. Pat. No. 9,304,102, issued Apr. 5, 2016, incorporated by reference herein (hereinafter, "Day et al."), describes amperometric sensors that include an electrically conductive active electrode comprising at least one molybdate or tungstate compound. The sensors described in Day et al. are highly responsive to $NO_X$ levels at desirable temperatures (e.g., 500-600° C.), and, in some instances, are highly responsive to both $NO_X$ and $NH_3$. The molybdate and tungstate active electrode compositions described in Day et al., when applied to an oxygen ion ($O^{2-}$) conducting electrolyte, show enhanced catalytic activity for $O_2$ reduction in the presence of $NO_X$ and $NH_3$. The sensors of Day et al. detect $NO_X$ and $NH_3$ through a catalytic effect in which the reduction of oxygen in a gas sample or gas stream is catalyzed by the presence of $NO_X$ and $NH_3$ species on the surface of the active electrode. The sensors of Day et al. also are responsive to $NO_X$ and $NH_3$ in the presence of steam, carbon dioxide and sulfur oxides ($SO_X$), which are additional constituents of diesel exhaust streams.

Furthermore, as described in Patent Pub. No. US 2016/077044, published on Mar. 17, 2016, and incorporated by reference herein, selection of the molybdate and/or tungstate compound used in the active electrode(s), and/or selection of a current collector(s) layer applied over the active electrode(s) can be used to tailor the sensor such that it can be used to determine, for example, both the $NO_X$ and $NH_3$ concentrations in a gas sample (i.e., the amount of $NO_X$ and the amount of $NH_3$, rather than the total amount of $NO_X$ and $NH_3$).

In some instances it is desirable to fabricate sensors wherein the electrodes are located on the same side of the electrolyte membrane rather than located on opposite sides of the electrolyte. In such "surface electrode" arrangements, the electrodes are located on the same side of the sensor with respect to the electrolyte layer(s). An electrode (e.g., a counter electrode) is not buried beneath the electrolyte. Typically, such surface electrodes are located on the upper surface of the electrolyte layer such that both are exposed to the gaseous analyte sample or stream being analyzed.

The present disclosure is based, in part, on the surprising discovery that a passive, conductive, signal amplifying layer (hereinafter, a "SAL") located below, but not in contact with, the surface electrodes of an amperometric sensor surprisingly enhances signal strength and, in some instances, sensor selectivity with respect to one or more gas species. By way of example, the sensor electrodes can be located on the upper surface of an electrolyte, with the SAL located within or beneath the electrolyte. In alternative embodiments of the present disclosure one or both of the electrodes of an amperometric sensor comprise a current collecting layer located on the electrolyte layer and a catalyst layer is located over the current collecting layer.

Embodiments of the amperometric electrochemical sensors, sensor systems and detection methods described herein are adapted to detect target gas species in a gaseous analyte sample or stream using a surface electrode arrangement. Thus, instead of locating the electrodes on opposite sides of the sensor with respect to an electrolyte layer(s), the electrodes are located on the same side of the sensor with respect to the electrolyte layer(s). In some embodiments, a passive, conductive, signal amplifying layer, or SAL (further described herein), is also provided, spaced away from the sensors. The SAL is in conductive contact with the electrolyte layer and can be located, for example, on the side of the electrolyte layer opposite that of the electrodes e.g., between the electrolyte layer and a sensor substrate. The SAL can be fully encapsulated between the electrolyte layer and the substrate (see, e.g., FIG. 1), or only partially encapsulated (e.g., such that the outer edges of the SAL are not covered by the electrolyte or substrate). As yet another alternative, the SAL can be fully encapsulated within the electrolyte layer, spaced away from both the upper and lower surfaces of the electrolyte layer such that the SAL is not in contact with a substrate on which the electrolyte layer is located. In some instances the advantages provided by the SAL are greater when the distance between the SAL and the electrodes is minimized without being so small that shorting between an electrode and the SAL occurs.

The signal amplifying layer is passive in that it has no direct electrical connection to, or contact with the sensors, a biasing source or a current measuring device. In fact, in some embodiments the SAL is only in direct, conductive contact with the electrolyte layer and the substrate (which is typically non-conductive). All conductivity between the electrodes and the SAL is through the electrolyte layer of the sensor, and no other current or electrical bias is supplied to the SAL. Despite its passive nature, the inventors have found that the signal amplifying layer surprisingly and significantly enhances signal strength and, in some instances, sensor sensitivity to certain gas species.

While the present disclosure describes amperometric sensors incorporating a SAL therein, the use of a passive, conductive, signal amplifying layer can be applied to a variety of other amperometric sensors and sensor systems, as well as mixed potential sensors and sensor systems that employ surface electrodes. This includes, for example, the sensors and sensor systems described in U.S. Pat. No. 8,974,657 entitled "Amperometric electrochemical cells and sensors," U.S. Pat. Pub. No. 2009/0218220 published on Sep. 3, 2009, and Day et al. (U.S. Pat. No. 9,304,102). Each of the foregoing references is incorporated by reference herein.

The SAL can be made from any of a variety of conductive materials suitable for sensor fabrication. Suitable materials include, for example, Pt, Pd, Au, Ag, alloys of the foregoing metals (e.g., an alloy of Pt with Pd, Au and/or Au), and other conductive metals conductive ceramics or cermets. Platinum is particularly useful.

In some embodiments, the amperometric electrochemical sensors, sensor systems and detection methods described herein are adapted to detect one or more target gas species in a gaseous analyte sample or stream. In embodiments for detecting a single gas species (including detecting a combination of two or more related gas species such as the presence and/or concentration of $NO_X$), the sensor comprises at least one electrochemical cell. In embodiments for detecting two or more gas species, particularly for use in determining the concentrations of individual gas species, the sensors generally include at least two electrochemical cells. By way of example, a sensor comprising two electrochemical cells can be configured such that one of the cells exhibits an additive response to the gas species of interest and another cell exhibits a selective response to at least one of the gas species. Alternatively, a sensor comprising a single electrochemical cell can be operated under two or more distinct conditions (e.g., forward bias and reverse bias) in order to provide two or more response characteristics, as further described herein. In some embodiments, the two (or more) electrochemical cells of a sensor are completely separate structures, while in other embodiments the two (or more) electrochemical cells of a sensor share one or more components such as a common electrolyte layer, SAL, substrate, counter electrode or active electrode.

In general, each electrochemical cell of an amperometric surface electrode sensor according to embodiments of the present disclosure includes an electrically conductive active electrode, an electrically conductive counter electrode (in some instances referred to as a second active electrode), an electrolyte layer, and a SAL. The active and counter electrodes are located on the same side of the electrolyte layer, in spaced-apart relationship, such that oxygen ions are conducted across the surface of and within the electrolyte layer. In some instances the active and counter electrodes are in a side-by-side arrangement on the electrolyte layer. Alternatively, the active and counter electrodes can be formed in an interdigitated arrangement (e.g., as seen in FIG. 4G). In some embodiments, a current collector layer in electrical communication with the active electrode (e.g., in contact therewith) is also included, as well as, in some instances, a current collector layer in electrical communication with the counter (or second active) electrode. As discussed below, the current collector layer(s) can be applied on top of the electrode. Alternatively, the current collector layer(s) can be located between the electrode and the electrolyte layer, as also discussed below.

By way of example only, the amperometric sensors, systems and methods described herein can be used to detect target gas species such as $NO_X$ and/or $NH_3$ in the oxygen-containing environment of a combusted hydrocarbon fuel exhaust, using, at least in part, an electro-catalytic effect. By way of a more specific example, the amperometric sensors, sensor systems and detection methods can operate in combustion exhaust streams (e.g., exhaust from a diesel engine of a vehicle), with significantly enhanced sensitivity to both $NO_X$ and $NH_3$. In some instances, the sensor can be configured to enable differentiation and quantification of $NO_X$ and $NH_3$ concentrations.

Embodiments of the electrochemical sensors, sensor systems and methods described herein are configured as amperometric devices/methods which respond in a predictable manner when an adsorbed gas species (e.g., $NO_X$) changes the rate of oxygen reduction at an active electrode of the sensor, under the influence of a bias applied between the two electrodes, rather than relying on the decomposition of that gas species (e.g., the catalytic decomposition of $NO_X$) in order to sense target gas (e.g., $NO_X$) concentration. A change in oxygen reduction current, caused by the presence of adsorbed $NO_X$, is used to detect the presence and/or concentration of $NO_X$ in oxygen-containing gas sample or stream. This mechanism is extremely fast and produces a current greater than what is possible from the reduction of $NO_X$ alone. Further, this catalytic approach has been demonstrated to extend to $NH_3$.

In some embodiments, each electrochemical cell of the amperometric ceramic electrochemical sensor comprises: an electrolyte layer comprising a continuous network of a material which is ionically conducting at an operating temperature of about 400 to 700° C.; a counter electrode layer which is electrically conductive at an operating temperature of about 400 to 700° C.; and an active electrode layer which is electrically conductive at an operating temperature of about 400 to 700° C. The active electrode layer is operable to exhibit a change in charge transfer in the presence of one or more target gas species and comprises a molybdate or tungstate compound, typically in combination with other materials such as an electrolyte and a metal. The electrode layers are located on the same side of the electrolyte layer, but are not in physical contact with one another (i.e., they are spaced apart). Embodiments of the electrochemical cells are operable to exhibit conductivity to oxygen ions at an operating temperature of about 400 to 700° C. When bias is applied between the electrodes, the electrochemical cell(s) generates an electrical signal as a function of target gas concentration in an oxygen-containing gas stream, in the absence of oxygen pumping currents.

In some embodiments, the electrochemical cell(s) further includes a current collector layer which is electrically conductive at an operating temperature of about 400 to 700° C., wherein the current collector layer is in electrical communication with (e.g., located on the surface of) the active electrode layer(s). The current collector layer is more electrically conductive than the active electrode layer, particularly at an operating temperature of about 400 to 700° C. The purpose of the current collector layer is to augment the electrical conductivity of the active electrode. However, in some embodiments, the current collector layer can also be chosen such that it also manipulates the catalytic and electrochemical reactions occurring at the active electrode, thereby providing reduced or enhanced sensitivity to one or more gas species of interest (e.g., NO, $NO_2$ or $NH_3$). In these embodiments, the combination of the active electrode and the current collector layer can be considered a two-layer active electrode.

The sensors described herein can be fabricated to have the ability to detect, for example, NO, $NO_2$ and $NH_3$, including at levels as low as 3 ppm and/or to exhibit response times as fast as 50 ms, allowing for better system controls or even engine feedback control. When configured to operate in a temperature range of 400 to 700° C., the $NO_X$ and $NH_3$ responses of some embodiments are greater than the sensitivity to variable background exhaust gases.

While the sensors, sensor systems and detection methods described herein have applicability to the detection of $NO_X$ in diesel exhaust systems, including exhaust systems found in heavy duty trucks and stationary generators, the same are also useful in a wide range of other applications in which rapid response to low levels of $NO_X$ and/or $NH_3$ is desired, particularly in oxygen-containing gas streams or samples. Examples include diesel generator sets, large-scale stationary power generators, turbine engines, natural gas fired boilers and even certain appliances (e.g., natural gas powered furnaces, water heaters, stoves, ovens, etc.). The sensors, sensor systems and detection methods are particularly useful in sensing low levels of $NO_X$ in the presence of fixed or variable concentrations of other gases, such as $O_2$, $CO_2$, $SO_X$ (SO and/or $SO_2$), $H_2O$, and $NH_3$.

The various electrochemical sensors, sensor systems and detection methods will be described herein by reference to specific electrolyte, electrode, current collector and SAL compositions. However, the electrochemical sensors, sensor systems and detection methods described herein will yield beneficial results with a wide range of materials. It will be understood that the thicknesses depicted in the drawings are greatly exaggerated and therefore are not intended to be to scale. In addition, unless the context indicates otherwise, the terms "detect", "detection", and "detecting" are intended to encompass not only the detection of the presence of a target species but also sensing or measuring the amount or concentration of the target species.

In some embodiments having two or more electrochemical cells, the active electrode and/or current collector layer of a first electrochemical cell is exposed to two or more target gas species (e.g., $NO_X$ and $NH_3$) such that the target gas species change the amount of oxygen reduced within the first electrochemical cell proportional to their concentrations. As a result, the total concentration of the target gas species in a gas sample or stream can be correlated with the oxygen ion current through the first electrochemical cell at any given applied voltage bias and sensor temperature. The response of the first electrochemical cell of the sensor in this example is "additive" in that the measured current at a given voltage bias and temperature can be correlated with the combined total concentration of the target gas species (e.g., $NO_X$ and $NH_3$). The active electrode and/or current collector layer of the second electrochemical cell also is exposed to the two or more target species. However, the second electrochemical cell is configured and/or operated such that a first one of the target gas species (e.g., $NO_X$) measurably changes the amount of oxygen reduced within the second cell, while a second one of the target gas species (e.g., $NH_3$) has a significantly smaller effect (if any) on the amount of oxygen reduced within the second cell. Thus, the second electrochemical cell is "selective" with respect to a first one of the target gas species in that the measured current through the second electrochemical cell can be correlated with the concentration of the first target gas species (e.g., $NO_X$) while changes in the concentration of the second target gas species do not appreciably affect (if at all) the measured current through the second electrochemical cell. In this manner, the concentrations of the target gas species can be determined. Of course any number of electrochemical cells can be provided as part of a single sensor in order to, for example, detect more than two gas species.

FIG. 1 illustrates an exemplary amperometric sensor system (10) comprising a single electrochemical cell (20) (i.e., a sensor) as well as circuitry comprising a biasing source (40) and a current measuring device (50). It will be understood that some embodiments of sensor systems described herein comprise at least two electrochemical cells, and therefore the sensor system of FIG. 1 only depicts half of such a sensor system. FIG. 4F, for example, depicts a sensor generally comprising two electrochemical cells, each of which is similar in construction to the individual cell (20) of the sensor shown in FIG. 1, with the cells deposited onto a common substrate (428).

Figure 3:
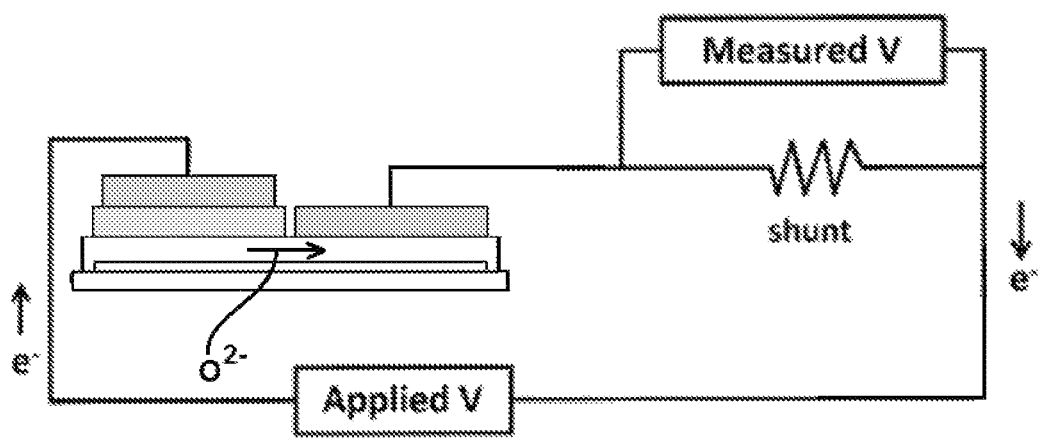
FIG. 3 is a schematic illustration of circuitry for use in conjunction with the sensors described herein, wherein the current measuring functionality (i.e., an ammeter) is provided by measuring the voltage drop across a shunt resistor with the voltage drop being proportional to the current flowing through the sensor.

Electrochemical cell (20) includes an active electrode (22), a counter electrode (26) and an oxygen-ion conducting electrolyte layer (24) on which the electrodes (22, 26) are located. By way of example, the electrically conductive active electrode (22) comprises at least one molybdate or tungstate compound. A passive, conductive, signal amplifying layer (or SAL) (27) is located beneath the electrolyte membrane (24), with a non-conductive substrate (28) supporting the SAL (27), as shown. In this embodiment, the SAL (27) is fully encapsulated by the electrolyte layer (24) and the substrate (28). Biasing source (40) is configured to apply a bias voltage between the two electrodes (22, 26), and current measuring device (50) is configured to measure the resulting current through sensor (20). Biasing source (40) can comprise any of a variety of power supplies or other devices suitable for applying a bias between the active electrode (22) and the counter electrode (26). The current measuring device (50) in FIG. 1 can comprise any of a variety of structures and devices known to those skilled in the art (or hereafter developed), such as an ammeter. As is well known to those skilled in the art, an ammeter can be provided by the combination of a shunt resistor and a voltmeter (as shown in FIG. 3).

Figure 2:
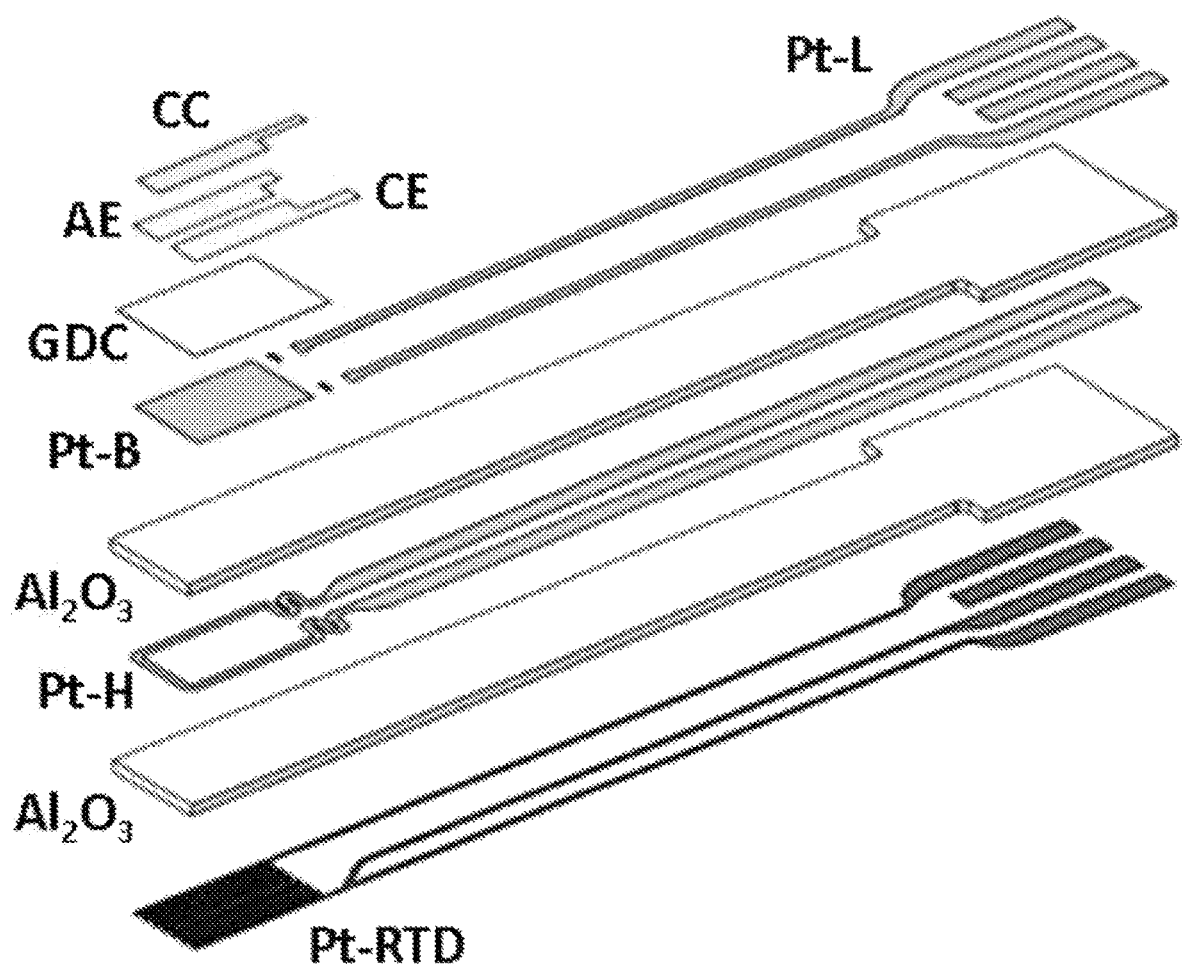
FIG. 2 is an exploded view of an electrochemical sensor design similar to that of FIG. 1 (without a biasing source or current measuring device), wherein the sensor includes a pair of substrate layers, a heater layer embedded between the substrate layers, a resistance temperature detector ("RTD") layer on a bottom substrate face, and multiple sequential layers on an upper substrate face: a signal amplifying layer (labeled "Pt-B"), an electrolyte membrane layer (labeled "GDC"), an active electrode layer (labeled "AE"), a counter electrode layer (labeled "CE"), and a current collector layer (labeled "CC") that covers the active electrode layer.

FIG. 2 is an exploded view of an electrochemical sensor similar to that of FIG. 1, with the addition several components. The sensor of FIG. 2 is fabricated by sequentially depositing the following layers onto an insulating substrate (i.e., the uppermost $Al_2O_3$ layer in FIG. 2): a signal amplifying layer ("Pt-B"); a single, common electrolyte layer ("GDC") that is deposited on the SAL; an active electrode layer ("AE") that is deposited on a portion of the upper surface of the electrolyte layer; a counter electrode layer (CE) that is deposited on a different portion of the upper surface of the electrolyte layer, spaced apart from the active electrode; and a first current collector layer ("CC") that is deposited on the upper surface of the active electrode layer. If desired, a second current collector layer can be deposited on the upper surface of the counter electrode layer. In the embodiment shown in FIG. 2, the sensor includes a second insulating $Al_2O_3$ substrate layer, along with a platinum resistive heater ("Pt-H") embedded between the substrate layers, and a platinum resistance temperature detector ("Pt-RTD", for monitoring sensor temperature) laminated to the bottom surface of the second substrate layer. Leads for the electrodes and current collectors ("Pt-L") are also shown along with leads for the Pt-H and Pt-RTD, are also depicted.

Returning to FIG. 1, when the current collector (36) is exposed to an oxygen-containing gas and a voltage bias is applied between the electrodes (22, 26), with electrochemical cell (20) heated to a suitable operating temperature, oxygen molecules are reduced at the active electrode (22). The presence of one or more target gas species (e.g., $NO_X$ and/or $NH_3$) will affect the amount of oxygen reduced at the active electrode (22), proportional to the target species concentrations. The resulting oxygen ions are conducted across and through the electrolyte membrane (24) to counter electrode (26), whereat the oxygen ions are oxidized to reform $O_2$ and generate a measurable current. The SAL (27) provides a lateral current path for electron transport beneath the electrolyte. As explained above, it is believed that the SAL (27) enhances the transport of oxygen ions from one electrode to the other. Under a forward bias, the SAL (27) provides an interface with the electrolyte layer whereat oxygen ions from the active electrode (22) are converted into electrons. These electrons are then transported through the SAL (27) to the region beneath the counter electrode (26), and then react with oxygen to form oxygen ions at the SAL/electrolyte interface. These oxygen ions are then transported through the electrolyte layer to the counter electrode (26). Thus, the SAL (27) provides an additional (and faster) pathway for the transport of oxygen ions from one electrode to the other through the electrolyte. However, it should be understood that it is electrons and not oxygen ions that are transported through the SAL.

In some sensor embodiments (including those used in the examples further described herein), the electrolyte layer is porous. In other embodiments the electrolyte layer is dense (no through porosity). In the embodiment shown in FIG. 1, electrolyte membrane (24) extends over the sides of the SAL (27) such that the SAL (27) is fully encapsulated between the electrolyte membrane (24) and the substrate (28). In other embodiments, e.g. FIGS. 7 and 8, the SAL is not fully encapsulated. It will therefore be understood that the full encapsulated SAL (27) in the embodiment of FIG. 1 can be replaced by the SAL arrangement shown in FIGS. 7 and 8 (i.e., the electrolyte does not extend over the entire periphery of the SAL). As used herein, "fully encapsulated" means that the SAL is surrounded by the electrolyte layer and substrate, or by the electrolyte layer alone (i.e., the SAL is not in contract with the substrate, but rather a portion of the electrolyte layer is located between the SAL and the substrate).

Embodiments of the sensors described herein include a substrate on which the electrochemical cell(s) is fabricated or otherwise supported, thereby providing mechanical support for the sensor. The substrate is generally non-conductive (i.e., insulating). The substrate may comprise any suitable insulating material such as an insulating ceramic material (e.g., aluminum oxide) or a metal or cermet material coated with an insulating material. In one embodiment, the sensor includes a zirconia substrate, more specifically, an yttrium-stabilized zirconia (YSZ) substrate.

Alternatively, the substrate may comprise a semiconducting material such as silicon or silicon carbide, with the components of the electrochemical cell(s) fabricated on the surface of the substrate using semiconductor fabrication techniques.

In embodiments wherein the active electrode comprises a molybdate and/or tungstate compound, any of a variety of molybdate and/or tungstate compounds can be used. Suitable compounds include those having the formula $A_X(Mo_{(1-Z)}W_Z)_YO_{(X+3Y)}$, wherein X and Y are each independently selected integers from 1 to 5, $0 \leq Z \leq 1$, and A is one or more ions that form binary compounds with Mo and/or W. By way of more specific example, A is one or more of Mg, Zn, Ni, Co, Fe, Mn, Cu, Ca, Sr, Ba, and Pb. In some embodiments, X and Y are both 1, and Z is 0. Particular examples of such molybdate compounds include: $MgMoO_4$, $ZnMoO_4$, $NiMoO_4$, $CoMoO_4$, $FeMoO_4$, $MnMoO_4$, $CuMoO_4$, $CaMoO_4$, $SrMoO_4$, $BaMoO_4$, and $PbMoO_4$. In other embodiments, X and Y are both 1, and Z is 1. Particular examples of such tungstate compounds include: $MgWO_4$, $ZnWO_4$, $NiWO_4$, $CoWO_4$, $FeWO_4$, $MnWO_4$, $CuWO_4$, $CaWO_4$, $SrWO_4$, $BaWO_4$, and $PbWO_4$.

Active electrodes comprising at least one molybdate or tungstate compound may have a variety of specific compositions, including, for example:
  (a) a molybdate compound ($A_XMo_YO_{(X+3Y)}$) or a tungstate compound ($A_XW_YO_{(X+3Y)}$), including, for example, an active electrode comprising more than 30%, more than 50%, more than 80% or even more than 90% (by volume) of the molybdate or tungstate compound;
  (b) one or more compounds having the formula $A_X(Mo_{(1-Z)}W_Z)_YO_{(X+3Y)}$, wherein X and Y are each independently selected integers from 1 to 5, $0<Z<1$, and A is one or more of Mg, Zn, Ni, Co, Fe, Mn, Cu, Ca, Sr, Ba, and Pb;
  (c) a composite mixture of two or more compounds chosen from the group consisting of molybdate and tungstate compounds, such as a composite mixture of at least one molybdate compound and at least one tungstate compound;
  (d) a composite mixture of one or more ceramic electrolyte materials and one or more of (a)-(c);
  (e) a composite made from a ceramic phase comprising one or more of (a)-(d), and a metallic phase (e.g., silver, gold, platinum, palladium, rhodium, ruthenium, iridium or alloys or mixtures thereof); or
  (f) a mixture of two or more of (a)-(e).

In some of the above embodiments, one or more additives or other materials may be added to the active electrode composition during fabrication, while in other embodiments no such additives are included.

The above-described molybdate and tungstate compounds, as well as the above-described solid solutions of molybdate and tungstate compounds, may be doped with one or more metals. In addition, or alternatively, one or more oxides may be added, such as manganese oxide, iron oxide, cobalt oxide, vanadium oxide, chromium oxide, tin oxide, niobium oxide, tantalum oxide, ruthenium oxide, indium oxide, titanium oxide, and zirconium oxide. When employed, these oxide additives may be present at an amount of between about 0.1 and 10% by volume in the active electrode layer, or between about 1 and 3% by volume in the active electrode layer.

As noted above, in some embodiments the active electrode(s) comprises a multi-phase composite of: (a) a molybdate and/or tungstate-containing ceramic phase (e.g., a molybdate, a tungstate, a solid solution or composite mixture of a molybdate and a tungstate, or a composite mixture of one or more of the foregoing and an electrolyte); and (b) a metallic phase (Ag, Au, Pt, Pd, Rh, Ru, Ir, or alloys or mixtures thereof). It should be kept in mind that the tungstate/molybdate ceramic phase of such composites may itself comprise more than one phase, such as a composite mixture of one or more molybdate and/or tungstate compounds and an electrolyte.

For the above-described multi-phase ceramic/metal composite materials, the amount of the metallic phase can range from about 0.1% to 10% by weight or about 30 to 70% by volume. In the multi-phase ceramic/metal composites having low levels of the metallic phase (e.g., about 0.1% to 10%, or about 1% to 5% by weight), Pt, Pd, Rh, Ru, or Ir (or alloys of mixtures thereof) are particularly useful. For the higher levels of the metallic phase (e.g., about 30% to 70%, or about 40% to 60% by volume), Ag, Au, Pt, Pd, Rh, Ru, or Ir (or alloys or mixtures thereof) may be used in order to improve electrical conductivity (although some sensitivity may be sacrificed).

As noted above, in some embodiments the active electrode(s) comprises a composite mixture of: (a) one or more ceramic electrolyte materials (e.g., gadolinium-doped ceria, "GDC," or samarium-doped ceria, "SDC"); (b) one or more molybdate and/or tungstate compounds; and, optionally, (c) a metallic phase (e.g., silver, gold, platinum, palladium, rhodium, ruthenium, iridium, or alloys or mixtures thereof). In these embodiments, the ceramic electrolyte material(s) in the active electrode (22) may be any of the electrolytes described below for electrolyte membrane (24), or another ceramic electrolyte material which conducts electricity through the conduction of oxygen ions (i.e., ionic conductivity rather than electronic conductivity). By way of example, suitable ceramic electrolytes for use in the active electrode include:
  (a) cerium oxide doped with one or more of Ca, Sr, Sc, Y, Pr, Nd, Pm, Sm, Eu, Gd, Tb, Dy, Ho, Er, Tm, Yb, or La;
  (b) zirconium oxide doped with one or more of Ca, Mg, Sc, Y, or Ce; and
  (c) lanthanum gallium oxide doped with one or more of Sr, Mg, Zn, Co, or Fe.

In more specific embodiments, the ceramic electrolyte used in the active electrode comprises cerium oxide doped with one or more of Ca, Sr, Sc, Y, Pr, Nd, Pm, Sm, Eu, Gd, Tb, Dy, Ho, Er, Tm, Yb, or La. For example, GDC or SDC is employed, in some instances in combination with Pt as the metallic phase.

The relative amounts of ceramic electrolyte and one or more molybdate/tungstate compounds in the composite mixtures described in the previous paragraph may be varied depending on, among other things, the nature of the application (e.g., the analyte gas stream/sample and surrounding environment), the configuration of the sensor and/or sensor system, the desired sensitivity, the identity of the target gas(es), etc. In some embodiments, the volumetric ratio of ceramic electrolyte(s) to molybdate/tungstate compound(s) in the active electrode is between about 1:9 and 9:1. In other embodiments, this ratio is between about 2.5:7.5 and 7.5:2.5, or even between about 4:6 and 6:4. And in still other embodiments this ratio is about 1:1. It should be pointed out that the foregoing volumetric ratios are based upon the ratio of the total volume of ceramic electrolytes to the total volume of molybdate and tungstate compounds in the active electrode layer in question. When the composite mixtures described in the preceding paragraph include a metallic phase, the nature and amount of the metallic phase may be any of the various metals and amounts described previously.

In still further embodiments employing a SAL, the active electrode material can be any of the materials described in previous sensor patents and published patent applications of Applicant previously incorporated by reference herein. The active electrode material can be electronically conductive or ionically conductive. In some instances, the active electrode material can be highly conductive such that a current collector layer is not required to achieve optimum signal strength, or minimally or moderately conductive such that a current collector layer is required to achieve optimum signal strength. (Signal strength is defined as the electrical current that results when a bias voltage is applied.)

By way of further example, as an alternative to the compositions described above that comprise a molybdate or tungstate compound, suitable active electrode materials for use in combination with a SAL for increasing signal strength include: a lanthanide manganite perovskite material, doped with Ca, Sr, Ba, Fe, Co, Ni, Cu, Zn, Mg or a mixture thereof; lanthanide ferrite perovskite material, doped with Ca, Sr, Ba, Mn, Co, Ni, Cu, Zn, Mg or a mixture thereof; lanthanide cobaltite perovskite material, doped with Ca, Sr, Ba, Mn, Fe, Ni, Cu, Zn, Mg or a mixture thereof; lanthanide nickelate perovskite material, doped with Ca, Sr, Ba, Mn, Fe, Co, Cu, Zn, Mg or a mixture thereof; lanthanide cuprate perovskite material, doped with Ca, Sr, Ba, Mn, Fe, Co, Ni, or a mixture thereof; a composite material comprising a mixture of ceramic and metallic phases (cermet), where the ceramic phase is a ceramic electrolyte material, for example, a zirconia-based electrolyte material, a ceria-based electrolyte material, a bismuth oxide-based electrolyte material or a lanthanum gallium oxide-based electrolyte material, or a mixture thereof, and the metallic phase comprises Ag, Pt, Pd, Rh, Ru, Ir or an alloy or mixture thereof; a composite material comprising a mixture of ceramic and metallic phases, wherein the ceramic phase is an insulator such as aluminum oxide, magnesium oxide, or another insulating ceramic material, and the metallic phase comprises Ag, Pt, Pd, Rh, Ru, Ir or an alloy or mixture thereof; a metallic electrode material comprising Ag, Pt, Pd, Rh, Ru, Ir or an alloy or mixture thereof; or a mixture comprising two or more of any of the above-mentioned sensing electrode materials.

In some embodiments, a current collector layer is provided for the active electrode layer(s) of the electrochemical cell(s), and, optionally, for the counter electrode layer(s). The current collector layer is more electrically conductive than the active electrode layer, and therefore augments the electrical conductivity of the active electrode so as to increase signal strength. And, in some embodiments the current collector layer also manipulates the catalytic and electrochemical reactions occurring at the underlying electrode such that reduced or enhanced sensitivity to one or more gas species of interest (e.g., NO, $NO_2$ or $NH_3$) is achieved.

For example, electrochemical cell (20) in FIG. 1 includes a current collector layer (36). Active electrode layer (22) is adjacent electrolyte membrane (24), while current collector layer (36) is located over active electrode layer (22). Current collector layer (36) has a higher electrical conductivity than the active electrode layer (22). In this particular embodiment, the current collector layer is configured as a full coverage current collector in that it covers at least about 90% of the top surface of the active electrode layer (22). In alternative embodiments, particular those in which the current collector is not configured to manipulate the catalytic and electrochemical reactions in order to reduce or enhance sensitivity to target gas species, the current collector can be configured to cover about 10-25% of the surface of the active electrode, as further described in Patent Pub. No. US 2016/077044.

As for the composition of the current collector layer, when the current collector is used merely to augment the electrical conductivity of the active electrode rather than manipulate the catalytic and/or electrochemical reactions at the underlying electrode, the current collector layer can comprise a noble metal such as platinum, palladium, gold, silver, or any other noble metal, an alloy of two or more noble metals, an alloy of one or more noble metals and one or more base metals, or a cermet of a noble metal and a ceramic electrolyte material.

Alternatively, the current collector layer can comprise a cermet comprising a metal (e.g., platinum or gold) and a ceramic phase such as GDC, SDC, zirconium-doped ceria ("ZDC"), yttrium stabilized zirconia ("YSZ"), scandium stabilized zirconia ("ScSZ"), or one of the other ceramic electrolytes mentioned as being suitable for use in the active electrode. The metal content of such cermet current collector layers should be sufficient to make the electrical conductivity of the current collector layer higher than that of the underlying electrode layer. As further discussed herein, such cermet current collectors can be used to manipulate the catalytic and/or electrochemical reactions of the electrochemical cell(s) of the sensor (e.g., to provide reduced or enhanced sensitivity to one or more gas species of interest).

For example, in some embodiments the cermet current collector(s) comprises platinum and a ceramic electrolyte (e.g., ScSz) in order to provide additive behavior with respect to $NO_X$ and $NH_3$, whereas cermet current collector(s) comprising gold and a ceramic electrolyte (e.g., GDC) provide selective behavior with respect to $NO_X$ in the presence of $NH_3$. In the case of cermet current collectors, particularly those used to manipulate the response of the electrochemical cells, the current collector can comprise about 40 to 80 vol %, or about 50 to 70 vol % of the metal phase (e.g., Pt or Au), with the remainder being the ceramic electrolyte phase (e.g., GDC or ScSz).

The counter electrode of the electrochemical cells of the sensors described herein can comprise any of a variety of materials, depending in part on the configuration of the electrochemical cell(s). For example, the counter electrode can comprise any of the compositions described above with respect to the current collector, such as a metallic material such as platinum or gold, or a conductive cermet comprising a metal (e.g., platinum or gold) and a ceramic phase (GDC, SDC, ZDC, YSZ or ScSZ). The counter electrode can also be any of the materials identified above for the active electrode. Other suitable materials for the counter electrodes of the sensors described herein include:

(a) a metal comprising Ag, Au, Pt, Pd, Rh, Ru, or Ir, or an alloy, mixture or cermet of any of the foregoing (e.g., a cermet comprising one or more of these metals, particularly Pt, and YSZ, ScSZ, GDC or SDC); and (b) various other conductive materials suitable for sensor fabrication, particularly materials which catalyze the re-oxidation of oxygen ions to molecular oxygen, including, for example, conductive perovskites, such as $(La,Sr)MnO_3$, $(La,Sr)CoO_3$, $(La,Sr)(Co,Fe)O_3$, $La(Ni,Fe)O_3$, $La(Ni,Co)O_3$, and related perovskite and brownmillerite structured materials.

In still further embodiments employing a SAL, the counter electrode material can be any of the materials described in the previous sensor patents and published patent applications of Applicant previously incorporated by reference herein. For example, as described in U.S. Pat. No. 8,974,657, suitable counter electrode materials for use in combination with a SAL for increasing signal strength include: a lanthanide manganite perovskite material, doped with Ca, Sr, Ba, Fe, Co, Ni, Cu, Zn, Mg or a mixture thereof; lanthanide ferrite perovskite material, doped with Ca, Sr, Ba, Mn, Co, Ni, Cu, Zn, Mg or a mixture thereof; lanthanide cobaltite perovskite material, doped with Ca, Sr, Ba, Mn, Fe, Ni, Cu, Zn, Mg or a mixture thereof; lanthanide nickelate perovskite material, doped with Ca, Sr, Ba, Mn, Fe, Co, Cu, Zn, Mg or a mixture thereof; lanthanide cuprate perovskite material, doped with Ca, Sr, Ba, Mn, Fe, Co, Ni, or a mixture thereof; or a metal material comprising Ni, Fe, Cu, Ag, Au, Pd, Pt, Rh, or Ir, or an alloy, a mixture or a cermet thereof.

It will be understood that in most instances the active and counter electrodes of an individual electrochemical cell will have different compositions and/or their respective current collector layers will have different compositions. For example, in some embodiments the active and counter electrode layers are identical, however, their respective current collector layers have different compositions. Because the current collector layers of an individual electrochemical call can be selected so as to manipulate the catalytic and/or electrochemical reactions of the cell, in some instances each "electrode" of an electrochemical cell can be considered to be the combination of an active (or "functional") electrode layer and a current collecting layer (if any). For example, a single electrochemical cell of a sensor can comprise first and second two-layer electrodes, each having an active (or "functional") layer and a current collecting layer, wherein at least one of the layers of the first electrode has a composition that is different from the corresponding layer of the second electrode. Accordingly, the first and second electrodes are different with respect to their catalytic and/or electro-catalytic responses to the gas species to be detected.

In alternative embodiments, the first electrode is a combination of an active electrode layer and an overlying current collecting layer, an active electrode layer only, or a current collecting layer only (i.e., a traditional counter electrode), and the second electrode is a different combination of an active electrode layer and/or current collecting layer.

As for the ionically-conducting electrolyte membrane of the electrochemical cells used in the sensors described herein, suitable materials include doped ceria electrolyte and doped zirconia electrolyte. More specific examples include gadolinium-doped ceria ($Ce_{1-X}Gd_XO_{2-X/2}$, wherein X ranges from approximately 0.05 to 0.40), samarium-doped ceria ($Ce_{1-X}Sm_XO_{2-X/2}$, where X ranges from approximately 0.05 to 0.40), yttrium-doped ceria (YDC), cerium oxide doped with other lanthanide elements, and cerium oxide doped with two or more lanthanide or rare earth elements. Still other suitable electrolyte materials include: fully or partially doped zirconium oxide, including but not limited to yttrium stabilized zirconia (YSZ) and scandium doped zirconia (ScSZ); other ceramic materials that conduct electricity predominantly via transport of oxygen ions; mixed conducting ceramic electrolyte materials; and mixtures of two or more of the foregoing. In addition, an interfacial layer of GDC, SDC or another suitable electrolyte material may be provided between the electrolyte membrane and one or both of the active and counter electrodes. Particularly suitable electrolyte materials include GDC, SDC, YSZ and ScSZ.

As yet another alternative, the ceramic electrolyte material can be beta alumina, sodium zirconium phosphate, lithium silicate, lithium aluminum silicate, or any alkali-ion conducting electrolyte material.

As mentioned previously, some embodiments of the sensors and sensor systems described herein generally comprise at least two electrochemical cells, wherein the first cell is configured (or operated) so as to provide an additive response with respect to two or more target gas species of interest (e.g., $NO_X$ and $NH_3$) and the second cell is configured (or operated) so as to provide a selective response with respect to a first one of the target gas species but not a second one of the target gas species. For NO and $NH_3$ sensing, for example, using the above-described active electrode materials, a sensor can be constructed with two electrochemical cells having different active electrodes: one that is sensitive to both $NO_X$ and $NH_3$ and one that is sensitive only to $NO_X$ (with little or no sensitivity to $NH_3$). Total $NO_X$ plus $NH_3$ concentration can be quantified by measuring current when applying a bias to the first electrochemical cell, the NO concentration can be quantified by measuring current when applying a bias to the second electrochemical cell, and the $NH_3$ concentration can be calculated by subtraction (total $NO_X$ plus $NH_3$ concentration minus $NO_X$ concentration). Thus, both $NO_X$ and $NH_3$ can be measured in a single sensor. The two electrochemical cells can be physically combined into one structure (e.g., with a common electrolyte layer, common SAL, common substrate and, optionally, common counter electrode), or two physically separate electrochemical cells may be fabricated.

As yet another alternative, a sensor can be constructed with two electrochemical cells having different current collector materials and the same or different active electrode materials, such that one cell is sensitive to both $NO_X$ and $NH_3$, and the other cell is sensitive only to $NO_X$. Total NO plus $NH_3$ concentration can be quantified by measuring current when applying a bias to the first electrochemical cell, the NO concentration can be quantified by measuring current when applying a bias to the second electrochemical cell, and the $NH_3$ concentration can be calculated by subtraction. Thus, both NO and $NH_3$ can be measured in a single sensor. As before, the two electrochemical cells can be physically combined into one structure, or two physically separate electrochemical cells may be employed.

Yet another alternative is a sensor constructed with two electrochemical cells having active electrodes of the same or similar composition, with or without associated current collectors of the same or similar composition, and the sensor can be operated with forward bias (i.e., from active electrode to counter-electrode) applied to one electrochemical cell to detect and quantify total NO plus $NH_3$, and with reverse bias (i.e., from counter electrode to active electrode) applied to the second electrochemical cell to detect and quantify either NO or $NH_3$ (with the other concentration calculated by subtraction). Thus, both NO and $NH_3$ can be measured in a single sensor. As before, the two electrochemical cells can be physically combined into one structure, or two physically separate electrochemical cells may be employed. Similarly, in some embodiments a single electrochemical cell is operated with forward and reverse bias (e.g., alternating between the two), wherein the response characteristics are different in the two biasing modes (e.g., additive in one biasing direction, and selective in the other).

In another alternative embodiment, a sensor can be constructed with two electrochemical cells, each having an active electrode of the same or different composition, with or without associated current collectors of the same or similar composition, and the sensor can be operated such that one cell is operated with forward bias (i.e., from active electrode to counter-electrode) to detect and quantify total $NO_X$, and the second cell operated with reverse bias (i.e., from counter electrode to active electrode) to detect and quantify $NH_3$. In this instance, one cell is selective to $NO_X$ and the other cell is selective to $NH_3$. Thus, both $NO_X$ and $NH_3$ can be measured in a single sensor. As before, the two electrochemical cells can be physically combined into one structure, or two physically separate electrochemical cells may be employed.

As mentioned previously, certain current collector layers are adapted to manipulate the catalytic and electrochemical reactions occurring in the sensor such that reduced or enhanced sensitivity to one or more gas species of interest (e.g., NO, $NO_2$ or $NH_3$) is achieved in the electrochemical cells. This is particularly useful when a surface electrode arrangement is employed for the electrochemical cell(s), with a full coverage (90% or more) current collector over at least the active electrode layer. Nevertheless, in such embodiments having two or more electrochemical cells, the cells can be configured so as to share a common substrate and, in some instances, a common electrolyte layer and/or a common counter electrode layer. FIGS. 4A-H depict such sensor arrangements. It will be understood, however, that the arrangements shown in FIGS. 4A-H can also be used for embodiments wherein only the material of the active electrodes controls the electrochemical cell behavior. In these instances the current collector layers can be omitted (if the active electrode layer is sufficiently conductive) or the current collector layers can be configured as a non-full coverage current collector (e.g., as a grid or mesh). It should be noted that the biasing source and current measuring device are not included in FIGS. 4A-H.

Figure 4A:
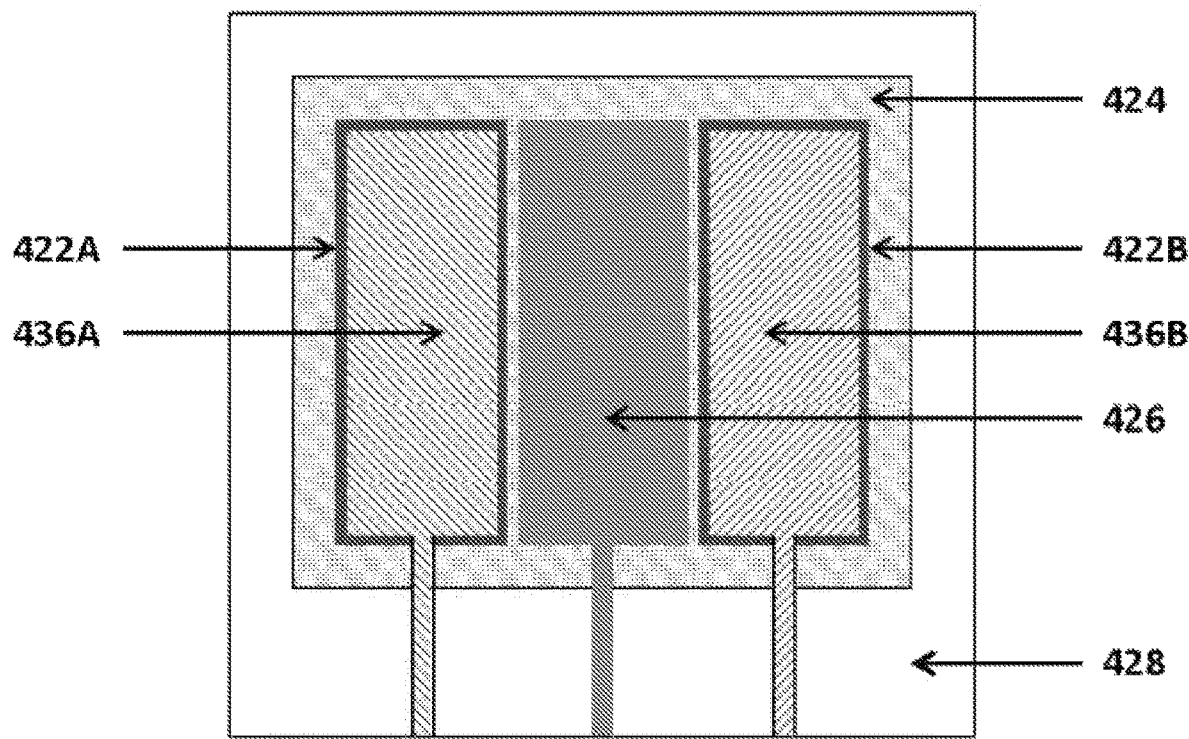
FIG. 4A and FIG. 4B are top and cross-sectional schematic views, respectively, of yet another alternative embodiment of a sensor system comprising two electrochemical cells having a common electrolyte layer and a common counter-electrode layer located between the two active electrode layers on the same side of the electrolyte layer (also referred to as a surface electrode sensor), along with a signal amplifying layer encapsulated between the electrolyte layer and the supporting substrate.
Figure 4B:
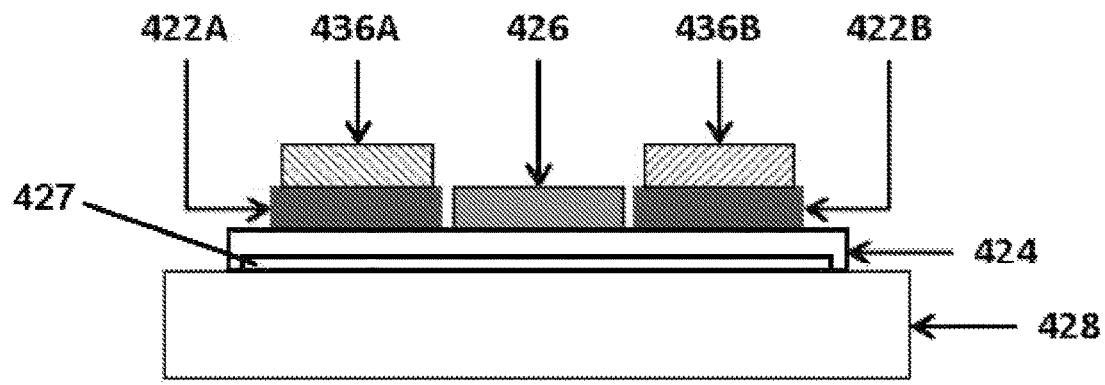

In the example depicted in FIGS. 4A and 4B, a sensor comprising two electrochemical cells is fabricated by sequentially depositing the necessary layers onto an appropriate insulating substrate (428): a single, common SAL (427); a single, common electrolyte layer (424) deposited over the SAL; a first active electrode layer (422A) that is deposited on a portion of the electrolyte layer surface; a second active electrode layer (422B) that is deposited on a different portion of the electrolyte layer surface; a single, common counter-electrode layer (426) that is deposited on a different portion of the electrolyte layer in close proximity to the first and second electrode layers (e.g., between the first and second active electrode layers) thus defining two electrochemical cells; a first current collector layer (436A) that is deposited on the first active electrode layer; and a second current collector layer (436B) that is deposited on the second active electrode layer.

Figure 4C:
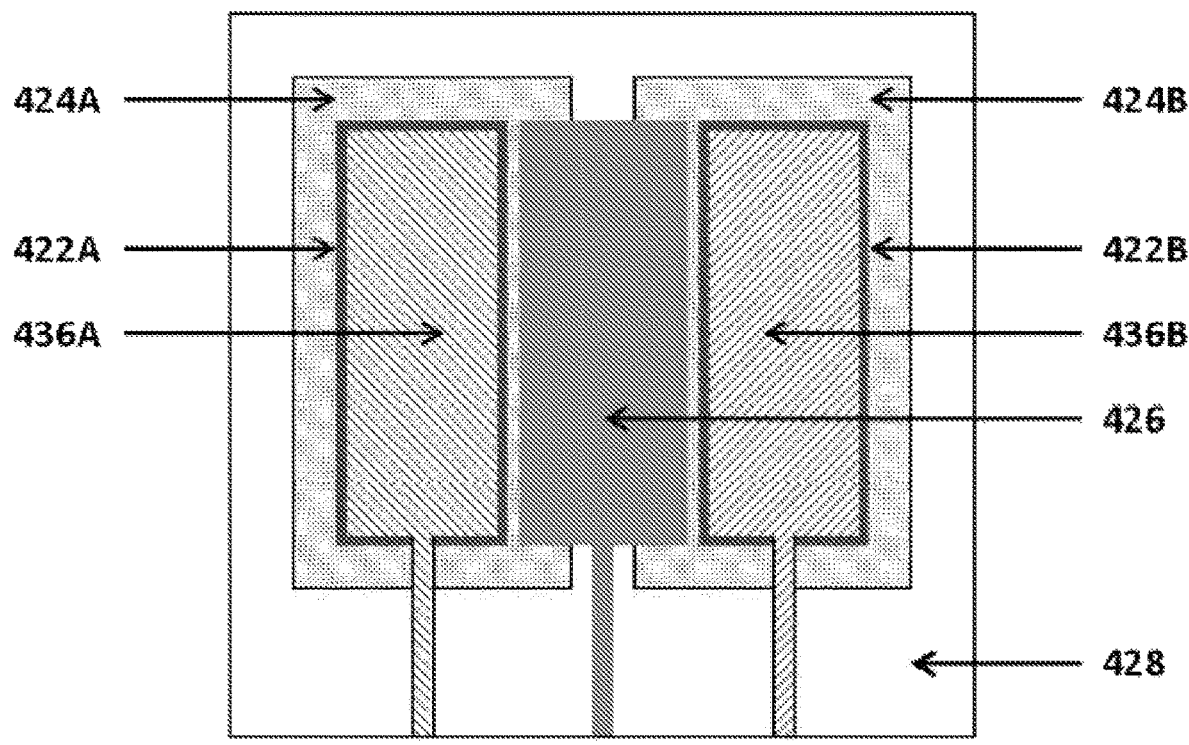
FIG. 4C and FIG. 4D are top and cross-sectional schematic views, respectively, of an alternative embodiment of a surface electrode sensor system comprising two electrochemical cells having separate electrolyte layers and a common counter-electrode layer located between the two active electrode layers, along with a signal amplifying layer encapsulated between the electrolyte layer and the supporting substrate.
Figure 4D:
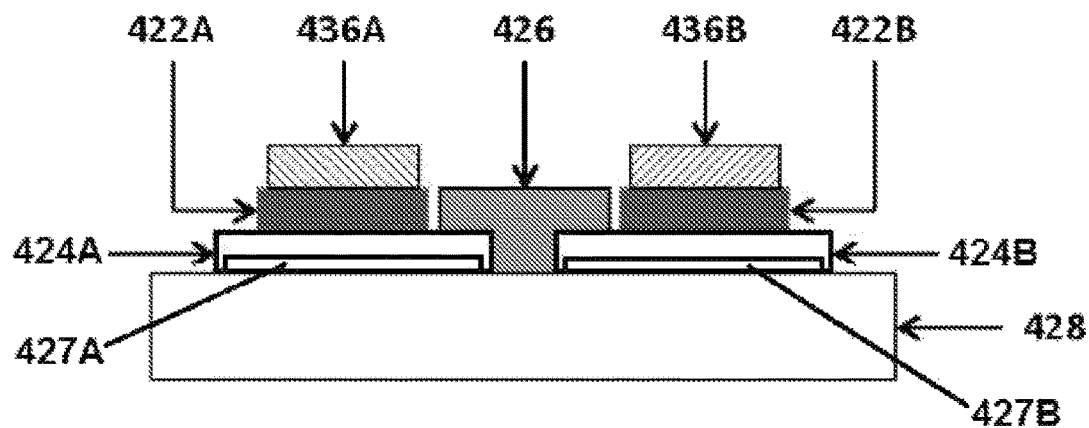

In the example depicted in FIGS. 4C and 4D, a sensor comprising two electrochemical cells is fabricated by sequentially depositing the necessary layers onto an appropriate insulating substrate (428): a first SAL (427A) that is deposited on one area of the insulating substrate; a second SAL (427B) that is deposited on a second area of the insulating substrate; a first electrolyte layer (424A) that is deposited over the first SAL (427A); a second electrolyte layer (424B) that is deposited over the second SAL (427B); a first active electrode layer (422A) that is deposited on a portion of the first electrolyte layer; a second active electrode layer (422B) that is deposited on a portion of the second electrolyte layer; a single, common counter-electrode layer (426) that is deposited on both the first and second electrolyte layers (and an area of the insulating substrate between the first and second electrolyte layers) in close proximity to and between the first and second electrode layers (thus defining two electrochemical cells); a first current collector layer (436A) that is deposited on the first active electrode layer; and a second current collector layer (436B) that is deposited on the second active electrode layer.

Figure 4E:
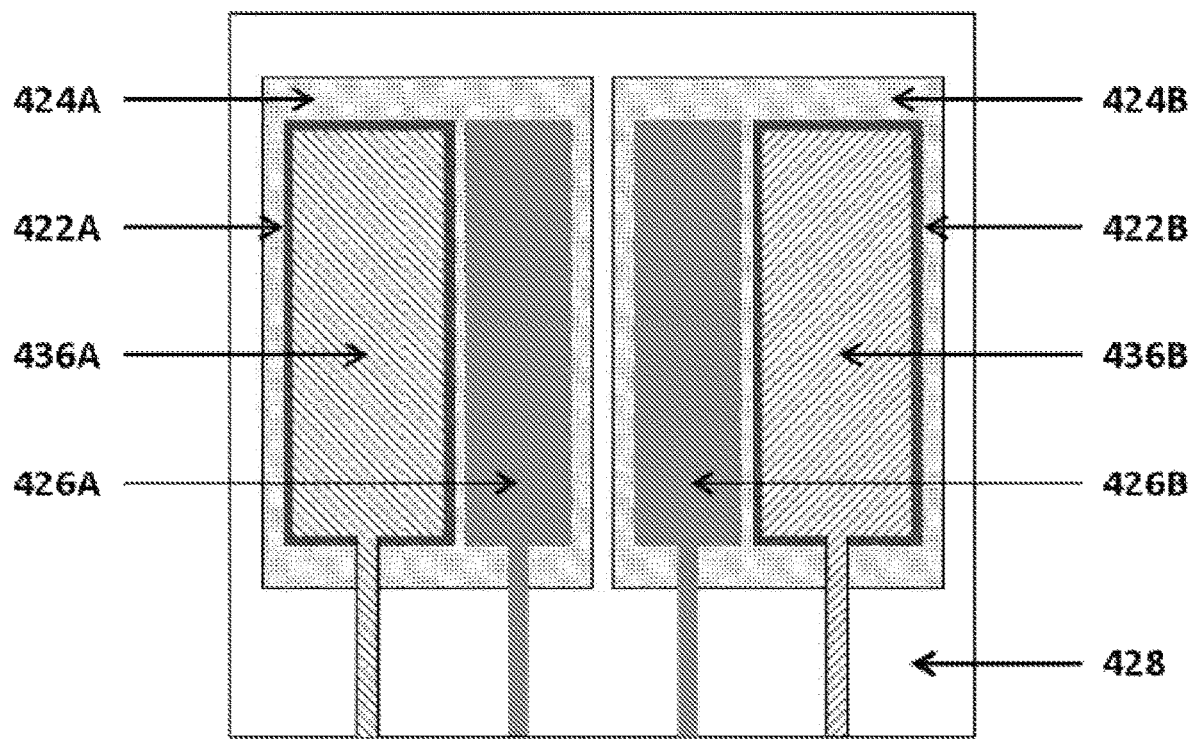
FIG. 4E and FIG. 4F are top and cross-sectional schematic views, respectively, of another alternative embodiment of a surface-electrode sensor system comprising two electrochemical cells having separate electrolyte layers and separate counter-electrode layers, along with a signal amplifying layer encapsulated between the electrolyte layer and the supporting substrate.
Figure 4F:
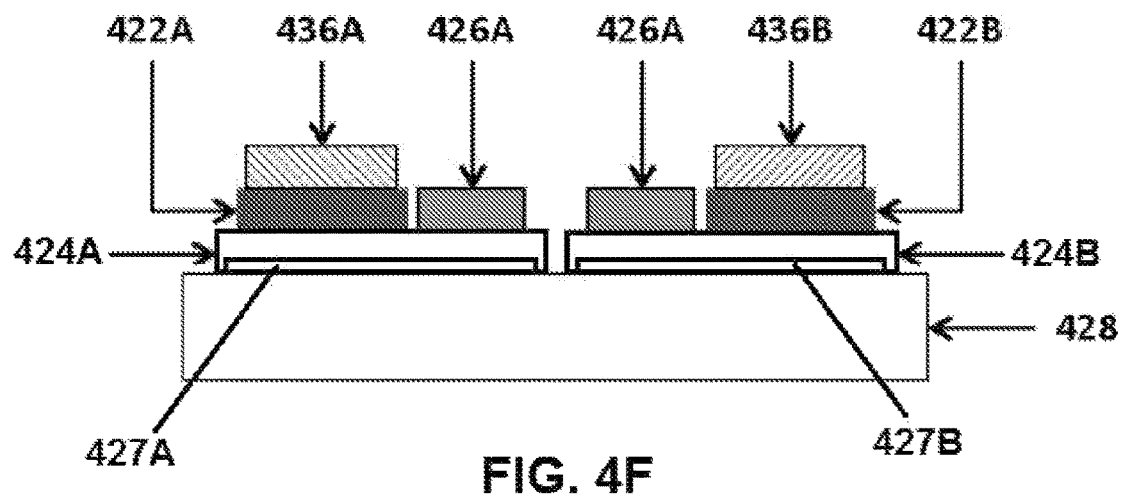
Figure 4G:
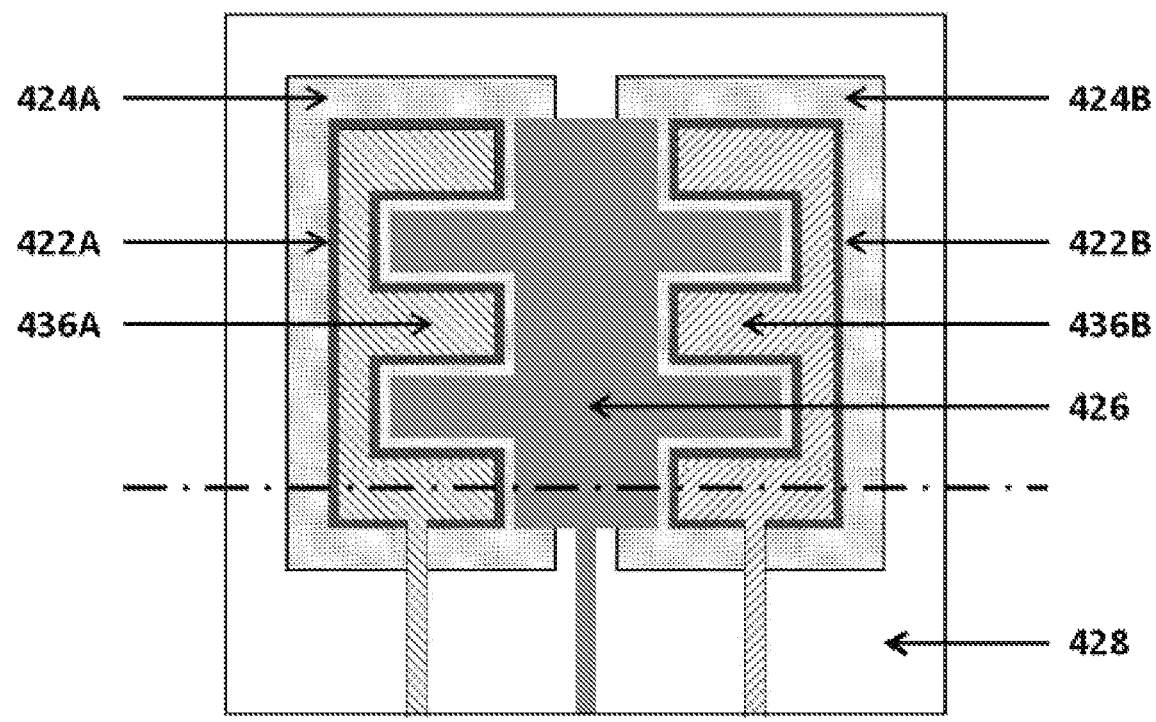
FIG. 4G and FIG. 4H are top and cross-sectional schematic views, respectively, of yet another embodiment of a surface-electrode sensor system having separate electrolyte layers and a common counter-electrode layer, wherein the electrodes have an interdigitated configuration, along with a signal amplifying layer encapsulated between the electrolyte layer and the supporting substrate.

In the example depicted in FIGS. 4E and 4F, a sensor comprising two electrochemical cells is fabricated by sequentially depositing the necessary layers onto an appropriate insulating substrate (428): a first SAL (427A) that is deposited on one area of the insulating substrate; a second SAL (427B) that is deposited on a second area of the insulating substrate; a first electrolyte layer (424A) that is deposited over the first SAL (427A); a second electrolyte layer (424B) that is deposited over the second SAL (427B); a first active electrode layer (422A) that is deposited on a portion of the first electrolyte layer; a second active electrode layer (422B) that is deposited on a portion of the second electrolyte layer; a first counter-electrode layer (426A) that is deposited on the first electrolyte layer in close proximity to the first electrode layer (thus defining a first electrochemical cell); a second counter-electrode layer (426B) that is deposited on the second electrolyte layer in close proximity to the second electrode layer (thus defining a second electrochemical cell); a first current collector layer (426A) that is deposited on the first active electrode layer; and a second current collector layer (436B) that is deposited on the second active electrode layer.

Figure 4H:
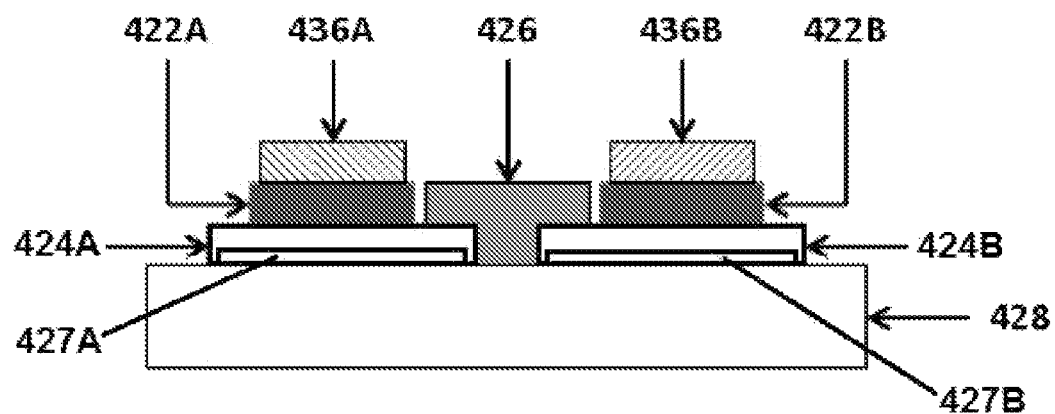

The example depicted in FIGS. 4G and 4H is similar to that of FIGS. 4C and 4D. In the embodiment of FIGS. 4G and 4H, however, the active and counter electrodes are interdigitated, thereby increasing the effective area of the surface electrodes while minimizing the gap between the electrodes.

Figure 5:
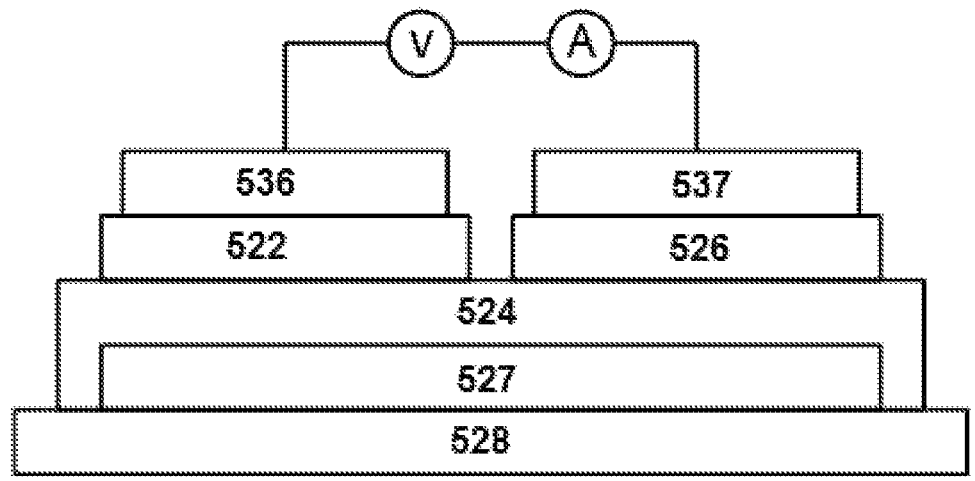
FIGS. 5-11 are schematic cross-sectional views of various additional sensor electrochemical cell (or sense element) embodiments that include a SAL, as further described herein.
Figure 6:
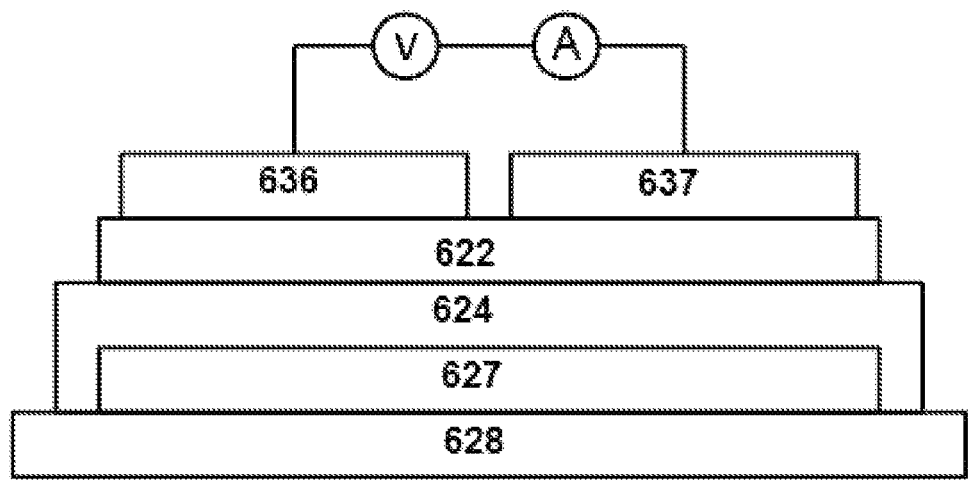

FIGS. 5-11 depict additional sensor embodiments (not to scale), in these instances of single sense elements (i.e., a single electrochemical cell), each of which includes a SAL (527, 627, 727, 827, 927, 1027, 1127). In FIGS. 5 and 6, the SAL (527, 627) is fully encapsulated between the electrolyte membrane (524, 624) and the substrate (528, 628). In FIGS. 7-11, the SAL (727, 827, 927, 1027, 1127) is not fully encapsulated between the electrolyte layer (724, 824, 924, 1024, 1124) and the substrate (728, 828, 928, 1028, 1128). Instead, the SAL is simply located between the electrolyte layer and the substrate, with portions of the SAL exposed. It will be understood that the SAL in the sensors of FIGS. 5 and 6 can be configured in this same way, and the SAL in the sensors of FIGS. 7-11 can alternatively be fully encapsulated as in FIGS. 5 and 6.

In FIG. 5, the sense element comprises an insulating substrate (528), a conductive signal amplifying layer (527), a ceramic electrolyte layer (524) that can be porous or dense, an active electrode layer (522), a counter electrode layer (526), and current collector layers (536, 537) that cover at least about 90% of the top surface of the active and counter electrode layers, respectively. The active and counter electrode layers (522, 526) can be the same or different compositions. Likewise, the current collector layers (536, 537) can be the same or different compositions. In general, if the active and counter electrode layers in the embodiments of FIGS. 5-8 are of the same composition, then the current collector layers are of different compositions (i.e., different from each other, or one of the current collector layers omitted). Likewise, if the current collector layers are of the same composition, then the active and counter electrode layers are of different compositions (i.e., different from each other). As noted in FIG. 5, a biasing voltage is applied between the two current collector layers, and the resulting current between the current collecting layers measures.

In FIG. 6, the sense element comprises an insulating substrate (628), a conductive signal amplifying layer (627), a ceramic electrolyte layer (624) that can be porous or dense, a single active electrode layer (622), and two current collector layers (636, 637) located on the single active electrode layer (622) in spaced-apart relationship. The two current collector layers (636, 637) are of different compositions. For example, in one embodiment the first current collector layer (636) comprises a cermet of Au and a ceramic phase (GDC, SDC, zirconium-doped ceria (ZDC), yttrium stabilized zirconia (YSZ), scandium stabilized zirconia (ScSZ), or one of the other ceramic electrolytes mentioned as being suitable for use in the active electrode), and the second current collector layer (637) comprises a cermet of Pt and a ceramic phase (GDC, SDC, zirconium-doped ceria (ZDC), yttrium stabilized zirconia (YSZ), scandium stabilized zirconia (ScSZ), or one of the other ceramic electrolytes mentioned as being suitable for use in the active electrode). By way of specific example, one current collector comprises Au/GDC and the other comprises Pt/ScSz. In the configuration shown in FIG. 6, one of the current collector layers (636, 637) and the portion of active electrode layer (622) therebeneath together provide an active electrode, while the other current collector layer and the portion of active electrode layer (622) therebeneath together provide a counter electrode (or a second active electrode). As noted in FIG. 6, a biasing voltage is applied between the two current collector layers, and the resulting current between the current collecting layers measures.

Figure 7:
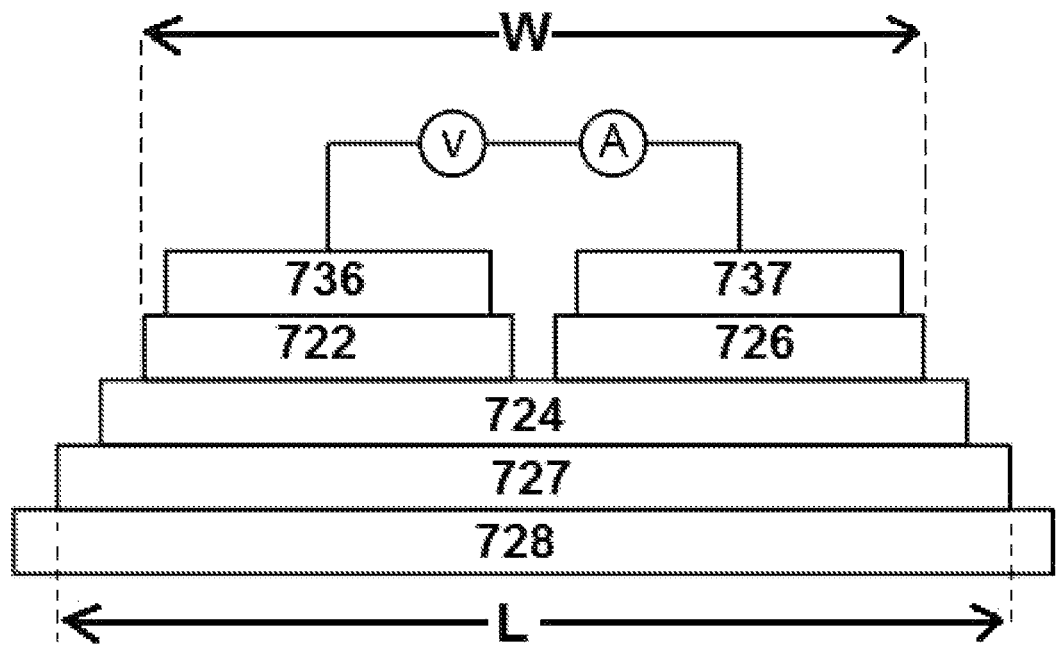

In FIG. 7 the sense element is similar to that of FIG. 5, only differing in that the SAL is not fully encapsulated between the electrolyte layer and the substrate. Thus, the sense element of FIG. 7 comprises an insulating substrate (728), a conductive signal amplifying layer (727), a ceramic electrolyte layer (724) that can be porous or dense, an active electrode layer (722), a counter electrode layer (726), and current collector layers (736, 737) that cover at least about 90% of the top surface of the active and counter electrode layers, respectively. Like the arrangement in FIG. 5, the active and counter electrode layers (722, 726) can be the same or different compositions, and the current collector layers (736, 737) can be the same or different compositions. Unlike FIG. 5, in the embodiment shown in FIG. 7, the SAL (727) is not fully encapsulated between the electrolyte membrane (724) and substrate (728). Instead, the SAL layer (727) is simply located between the electrolyte membrane layer and the substrate layer, as shown.

Figure 8:
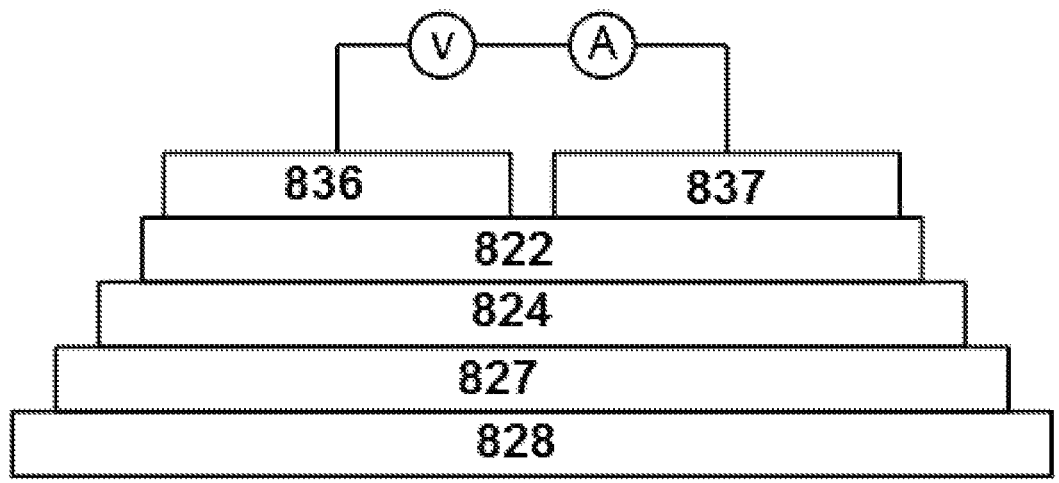

In FIG. 8 the sense element is similar to that of FIG. 6, only differing by the use of a SAL that is not fully encapsulated. Thus, the sense element comprises an insulating substrate (828), a conductive signal amplifying layer (827), a ceramic electrolyte layer (824) that can be porous or dense, a single active electrode layer (822), and two current collector layers (836, 837) located on the single active electrode layer (822) in spaced-apart relationship. The two current collector layers (836, 837) are of different compositions, and may be, for example, the compositions described above with respect to FIG. 6. In the configuration shown in FIG. 8 the SAL (827) is not fully encapsulated between the electrolyte membrane (824) and substrate (828). Instead, the SAL layer (827) is simply located between the electrolyte membrane (824) layer and the substrate layer.

It should also be pointed out that the designation of one electrode as the "counter electrode" and the other as the "active electrode" in the sensor embodiments described herein is, in some instances, arbitrary. For example, the direction of electronic and ionic current flow between the two electrodes can be changed by switching from one bias direction to the other. Thus, the counter electrodes in FIGS. 5-8, where present, can also be characterized as a second active electrode layer.

The various layers of the embodiments shown in FIGS. 5-8 can be any of the various compositions described herein. By way of specific examples, the substrate can be alumina, the SAL Pt, and the electrolyte layer GDC. The active electrode can be a molybdate or tungstate compound (e.g., $MgWO_4$ or $BaWO_4$) in combination with an electrolyte (e.g., GDC) and a metal (e.g., Pt). The counter electrode can be a metal (e.g., Pt or Au), a cermet of an electrolyte (e.g., GDC or ScSZ) and a metal (e.g., Pt or Au), or a molybdate or tungstate compound (e.g., $MgWO_4$ or $BaWO_4$) in combination with an electrolyte (e.g., GDC) and a metal (e.g., Pt). The current collectors can similarly be a metal (e.g., Pt or Au), or a cermet of an electrolyte (e.g., GDC or ScSZ) and a metal (e.g., Pt or Au). In some instances, a current collector is not provided over the counter electrode. In more specific embodiments, the current collector over the active electrode comprises a cermet chosen from Au/GDC, Pt/GDC, and Pt/ScSZ; and the counter electrode (without an overlying current collector) comprises a cermet chosen from Au/GDC, Pt/GDC, and Pt/ScSZ, wherein the metal used in the cermet of the counter electrode (Au or Pt) is different than the metal used in the cermet of the current collector of the active electrode (Pt or Au).

Figure 9:
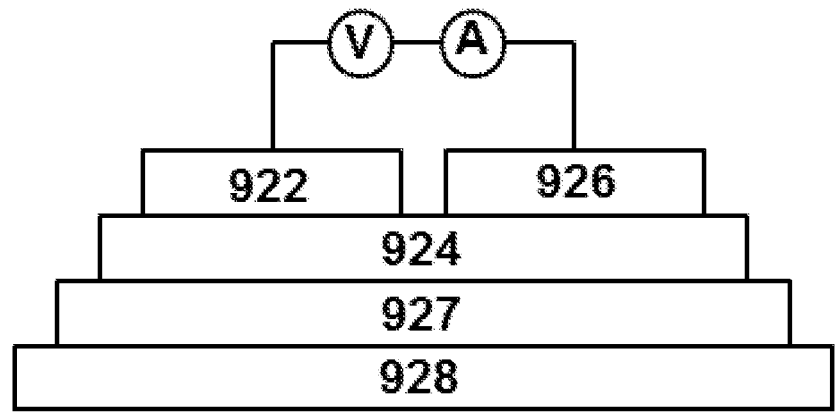

In still further alternative embodiments, the SAL can allow for the use of single layer electrodes rather than the combination of an active/counter electrode and current collecting layer. Furthermore, the SAL can allow for the use of certain components of the active electrode and electrolyte layers to be combined (which can alternatively be characterized as the elimination of the electrolyte layer beneath one or both of the electrodes) provided that the modified electrolyte layer includes a substantial amount of ceramic electrolyte material (e.g., greater than about 60 volume percent, or enough such that the electrolyte material is above its percolation limit and the non-electrolyte materials is below the percolation limit) so that the modified electrolyte layer active conducts electricity primarily via oxygen ions. In this instance, differentiation between the electrodes can be provided by having two different current collector materials. FIG. 9 depicts such an embodiment of a sense element employing a SAL (927).

In FIG. 9, the sense element comprises an insulating substrate (928), a conductive signal amplifying layer (927), a ceramic electrolyte layer (924) that can be porous or dense, a first electrode layer (922) located on a portion of the upper surface of the electrolyte layer (924), and a second electrode layer (926) located on another portion of the upper surface of the electrolyte layer (924) adjacent the first electrode layer (922). The first and second electrodes (922, 926) (e.g., an active electrode and a counter electrode) have different compositions and can comprise any of the various compositions described herein for an active electrode, a counter electrode or even a current collector.

While the electrolyte layer (924) can be, for example, doped ceria or doped zirconia electrolyte, it can alternatively be a modified electrolyte material comprising at least about 60% by volume of doped ceria or doped zirconia electrolyte (e.g., GDC, SDC, ZDC, YSZ, or ScSZ) in combination with: one or more of the molybdate or tungstate compounds described previously herein (e.g., $MgWO_4$ or $BaWO_4$); and/or one or more metals such as Pt, Pd, Rh, Ru, or Ir (or alloys or mixtures thereof). By way of one specific example, the modified electrolyte layer comprises: about 60% to about 95% by volume of a doped ceria or doped zirconia electrolyte (e.g., GDC, SDC, ZDC, YSZ, or ScSZ); and about 5% to about 40% of a molybdate or tungstate compound in combination with a metal chosen from the group consisting of Pt, Pd, Rh, Ru, and Ir.

By using a modified electrolyte layer in the embodiment of FIG. 9, the benefits of molybdate/tungstate compounds can be taken advantage of in the electrolyte layer rather than in an additional electrode layer. When such a modified electrolyte layer is used in the embodiment of FIG. 9, the electrodes (922, 926) should have different compositions. For example, one electrode can comprise a cermet containing platinum and an electrolyte (GDC, SDC, YSZ, ScSZ), while the other comprises a cermet containing gold and an electrolyte (GDC, SDC, YSZ, ScSZ).

Figure 10:
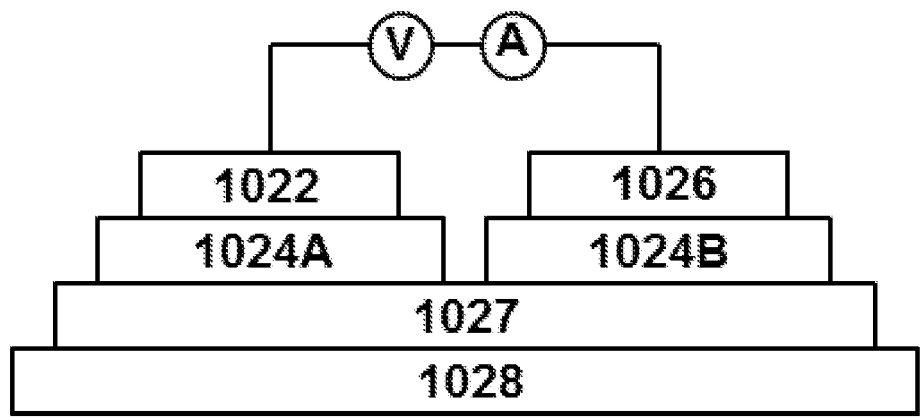

In additional embodiments, the SAL can allow for the bifurcation of the electrolyte into two adjacent layers, each located beneath one of the surface electrodes. In these instances, the lateral conduction between the electrodes under bias is solely through the SAL. The oxygen ions that would normally be conducted between the electrodes through the electrolyte layer are converted into electrons at the interface of the first electrolyte layer and the SAL. These electrons are then transported through the SAL and thereafter react with oxygen to form oxygen ions at the interface of the SAL and the second electrolyte layer. FIG. 10 depicts one such embodiment, wherein the sense element comprises an insulating substrate (1028), a conductive signal amplifying layer (1027), a first ceramic electrolyte layer (1024A) located on a portion of the SAL, a second ceramic electrolyte layer (1024B) located on another portion of the SAL adjacent the first electrolyte layer (1024A), a first electrode layer (1022) located on first ceramic electrolyte layer (1024A), and a second electrode layer (1026) located on the second ceramic electrolyte layer (1024B). The first and second electrodes (1022, 1026) (e.g., an active electrode and a counter electrode) have different compositions and can comprise any of the various compositions described herein for an active electrode, a counter electrode or even a current collector. The first and second electrolyte layers can be the same or different compositions, and can comprise, for example, doped ceria or doped zirconia electrolyte, or alternatively a modified electrolyte material as described above with respect to FIG. 9.

Figure 11:
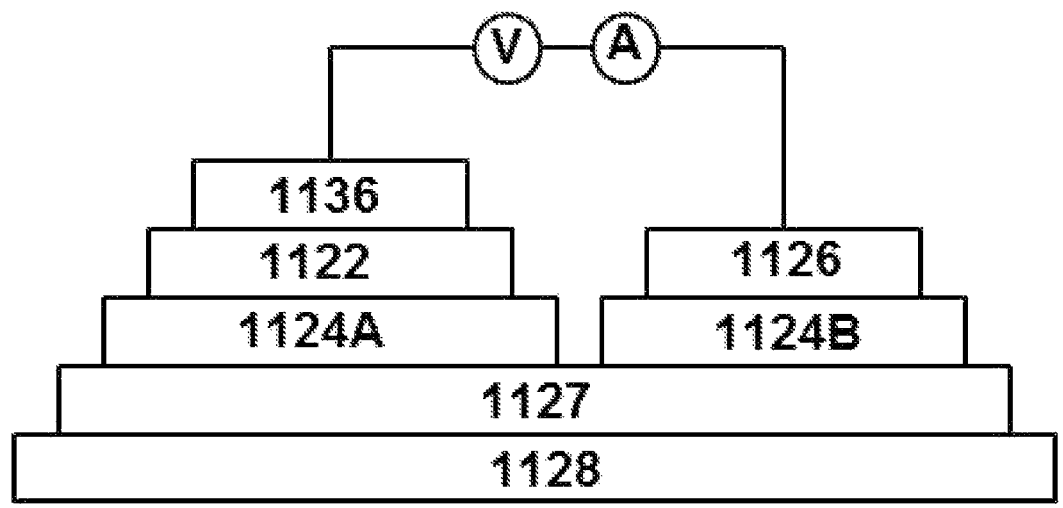

FIG. 11 depicts yet another alternative embodiment of a sense element employing a bifurcated electrolyte layer. In FIG. 11, the sense element comprises an insulating substrate (1128), a conductive signal amplifying layer (1127), a first ceramic electrolyte layer (1124A) located on a portion of the SAL, a second ceramic electrolyte layer (1124B) located on another portion of the SAL adjacent the first electrolyte layer (1124A), a first electrode layer (1122) located on first ceramic electrolyte layer (1024A), a current collector layer (1136) located on the first electrode layer (1122), and a second electrode layer (1126) located on the second ceramic electrolyte layer (1124B). The first and second electrodes (1122, 1126) (e.g., an active electrode and a counter electrode) have the same or different compositions and can comprise any of the various compositions described herein for an active electrode, a counter electrode or even a current collector. The first and second electrolyte layers can be the same or different compositions, and can comprise, for example, doped ceria or doped zirconia electrolyte, or alternatively a modified electrolyte material as described above with respect to FIG. 9. By way of example, the first electrolyte layer (1124A) comprises doped ceria or doped zirconia electrolyte, while the second electrolyte layer comprises a modified electrolyte material (e.g., includes a molybdate compound along with GDC or SDC) as described above with respect to FIG. 9.

Embodiments of the sensors described herein generally include a substrate, in combination with the described electrochemical cells, in order to provide mechanical support. The substrate may comprise any suitable insulating material, for example, an insulating ceramic material such as aluminum oxide, magnesium oxide, magnesium aluminate, mullite, steatite, or cordierite. Aluminum oxide is particularly useful as a substrate material. Devices also can be constructed with a metal or alloy as the substrate material (instead of an insulating material). In these instances, the metallic substrate itself would then serve as the signal amplifying layer. This would require deposition of an electrolyte material (or electrolyte containing active electrode material) directly onto the metallic substrate in such a way that an insulating layer is not created at the interface during deposition of the electrolyte, active electrode and current collector layers. For example, sputtering processes (or the like) can be used to deposit the various layers.

The sensors and sensor systems herein can be configured to be compatible with various application environments, and can include substrates with modifications to provide structural robustness, the addition of one or more heaters to control sensor temperature, and/or the addition of a resistance temperature detector ("RTD"), a thermistor, a thermocouple or other device to measure temperature and provide feedback to the electronic controller for temperature control. An alternative temperature measurement approach, based on the use of impedance of the electrolyte layer at a specific frequency, also can be used (this approach would require the addition of specific features to the sensor device architecture). Modifications can also be made to the overall sensor size and shape, external packaging and shielding to house and protect the sensor, and appropriate leads and wiring to communicate the sensor signal to an external device or application.

The sensor can optionally include a heater which is electrically isolated from the electrolyte and electrodes. In some embodiments, the heater comprises a resistive heater formed, for example, from a conductive metal such as, but not limited to, platinum, palladium, silver, or the like. The heater can, for example, be applied to or embedded in the substrate, or applied to the cell through another insulating layer such as an additional insulating layer (e.g., aluminum oxide). In still other embodiments, a temperature measurement mechanism is applied to the sensor to measure temperature and feed that back to the electronic controller to enable closed-loop temperature control. The temperature measurement mechanism, for example, is a resistance temperature device (RTD) made from a conductive metal or metal/ceramic composite with a high temperature coefficient of resistance (e.g., platinum or a platinum based cermet).

In specific embodiments such as that shown in FIG. 2, the electrochemical sensor is made using tape casting and screen printing techniques commonly used during the manufacture of multilayer ceramic capacitors and multilayer ceramic substrates. The first part of this process involves tape casting of aluminum oxide sheets (or tape). In the green state, via holes are cut into the substrate using a laser cutter or punch, providing electrical pathway connections from an embedded heater or other structures to the contact pads on an outer surface of the ceramic element. Platinum (or platinum based material) is screen printed onto one face of a green aluminum oxide tape in patterns that, after sintering, will provide a heater. Also in the green state, the SAL is screen printed onto one face of a green aluminum oxide tape.

In the various embodiments described herein, the SAL is generally a continuous, conductive layer configured to extend beneath at least about 50% of the surface electrodes, including spanning beneath the gap between the two electrodes. In other words, the SAL is located beneath the surface electrodes and has a size that is about 50% to about 120% of the combined size of the surface electrodes (including the gap between the electrodes). For example, as depicted in FIG. 7, the cross-sectional length (L) of the SAL (727) is about 120% of the edge-to-edge width (W) of the electrodes (722, 726). In FIGS. 5 and 6, the SAL size is approximately the same as the electrode area (including the gap between the surface electrodes).

The SAL can be made from a variety of conductive materials suitable for sensor fabrication. Suitable materials include Pt, Pd, Au, Ag, alloys of the foregoing metals (e.g., an alloy of Pt with Pd, Au and/or Au), or other conductive metal or ceramic material. Platinum is particularly useful.

Returning to the embodiment of FIG. 2, after formation of the SAL layer, multiple layers of green aluminum oxide tape are aligned and stacked such that the screen-printed heater layer is in the middle and the SAL is on the opposite face. The stack of green alumina tapes then is laminated by application of uniaxial pressure at slightly elevated temperature. The via holes are filled with conductive ink, such as platinum, and the stack is sintered at high temperature to consolidate the aluminum oxide substrate. A porous ceria-based electrolyte (GDC or SDC) layer (or other electrolyte material) is then applied over the SAL and onto the surrounding face of the substrate by screen printing and sintering. Platinum (or platinum based material) is screen printed onto the outer face of the sintered element, in patterns that, after sintering, will provide an RTD to enable a temperature measurement. Alternatively, another suitable material for an RTD may be applied in the green state prior to sintering of the aluminum oxide substrates and co-sintered therewith. A glass layer can be applied over the RTD and cured to protect the RTD in the application. Alternatively, both the heater and RTD layers can be embedded within the substrate in the green state and connections made with platinum vias (as described above), or only the platinum RTD can be embedded within the substrate, and the heater layer can be printed on the exterior surface and protected with a glass layer. Alternatively, the RTD can be omitted, and another means used for temperature measurement and control can be used.

Manufacture of the electrochemical cell or sensor is then completed by screen printing of the active and counter electrode layers (made of any of the compositions described herein) onto the electrolyte layer, followed by sintering of the electrode layers in order to anneal the electrode layers and promote adhesion. A current collector layer than can be applied in a similar manner. A porous ceramic coating, such as a zeolite or gamma alumina, can additionally be applied over the electrodes/current collector to protect these layers in the application and calcined to improve adhesion. It should be noted that multiple electrochemical cells or sensors can be made simultaneously with the above described process by array processing.

Sensor systems are formed, for example, by coupling one or more of the sensors described herein with one or more electronic controllers configured to controllably apply the bias voltage, control temperature (e.g., through pulse width modulation of the input voltage to the heater based on the sensor temperature measurement supplied to the controller). In some embodiments, the controller is configured to provide a conditioned sensor output, such as calibrated or linearized output.

Methods of detecting, sensing and/or monitoring the concentration of one or more target gas species such as $NO_X$ and/or $NH_3$ are also provided, employing any of the various sensors and sensor systems described herein. In these methods, a bias voltage is applied to the electrochemical cells of the sensor and the resulting current is measured. The measured current is correlated with the target gas species at a sensor temperature, based on previously compiled sensor data. In general, the measured current changes as the concentration of target gas species in the gas sample or stream increases. By using predetermined sensor response data, at any given sensor operating temperature and applied bias voltage, target gas species may be determined on the basis of the generated current through the sensor cell.

The sensors, sensor systems and methods described herein can also be adapted for detecting a variety of other gas species, including carbon monoxide (CO), methane ($CH_4$), ethanol ($C_2H_6$), hydrogen sulfide ($H_2S$), sulfur oxides ($SO_X$), hydrogen ($H_2$), refrigerants, oxygen ($O_2$), volatile organic compounds (VOC's) and other hydrocarbons. Various additional features and advantages of the amperometric sensors, sensor systems and methods will become evident from the devices and results obtained as described under the Examples that are described later.

As noted previously, sensors can be constructed with two active electrodes, effectively providing two different electrochemical cells, in order to provide for measurement of both $NO_X$ concentration and $NH_3$ concentrations. For the purposes of testing, exemplary sensors were fabricated as a single electrochemical cell and tested under conditions that would enable the design of dual $NO_X$/$NH_3$ sensors having multiple electrochemical cells. Through this testing, applicants have discovered multiple approaches for fabricating sensors for measuring both $NO_X$ and $NH_3$ concentrations. These approaches generally involve building and operating one electrochemical cell such that the cell exhibits an additive response with respect to $NO_X$ and $NH_3$ (i.e., the identical response to all three species), and building and operating a second electrochemical cell such that the cell exhibits a selective response with respect to $NO_X$ in the presence of $NH_3$ (i.e., identical response to NO and $NO_2$ and a diminished or no response to $NH_3$).

An additive response means that the magnitude of the signal provided by the electrochemical cell is proportional to the total combined concentration of the analytes (e.g., NO, $NO_2$ and $NH_3$) in the gas sample or gas stream being analyzed. Thus, in the amperometric sensors described herein, an individual electrochemical cell of a sensor which exhibits an additive response to NO, $NO_2$ and $NH_3$ will provide a signal which is proportional to the total, combined concentration of NO, $NO_2$ and $NH_3$. In other words, the electrochemical cell of the sensor exhibits approximately equal responses to NO, $NO_2$ and $NH_3$ such that approximately the same current is generated when that electrochemical cell is exposed to a given concentration of NO, $NO_2$ and $NH_3$ (e.g., approximately the same current is generated when the electrochemical cell is exposed to 20 ppm NO, 20 ppm $NO_2$ or 20 ppm $NH_3$). In particular, an individual electrochemical cell of a sensor is considered to be additive with respect to two or more analyte species when the sensitivity to each of those species is within a range of ±20% for a given concentration within the range of 10-200 ppm of the gas analyte species. As used herein, the sensitivity is the percent change in the current signal compared to the current signal in the absence of the analyte species. In some embodiments, the sensitivity to two or more analyte species of an additive electrochemical cell is within a range of ±10%, or even ±5%.

While one electrochemical cell of the sensor exhibits an additive response to two or more target gas species (e.g., $NO_X$ and $NH_3$), the other electrochemical cell of the sensor is minimally responsive or non-responsive to one of the target gas species (e.g., either $NO_X$ or $NH_3$)—i.e., a selective response. Selectivity is provided by either the configuration of the second electrochemical cell (e.g., the selection of the active electrode material and/or the current collector) and/or the mode of operation of the second electrochemical cell (e.g., direction of biasing). An electrochemical cell of a sensor is minimally responsive (i.e., selective) with respect to a particular analyte when the sensitivity for that analyte is less than 20% of the sensitivity to the other analyte(s) of interest at a given concentration within the range of 10-200 ppm. In some embodiments, the sensitivity to one analyte is less than 10% of the sensitivity to the other analyte(s), or even less than 5%. In one particular embodiment, when a first electrochemical cell of a sensor is additive with respect to $NO_X$ and $NH_3$, and the second electrochemical cell of the sensor is responsive to $NO_X$ but only minimally responsive or non-responsive to $NH_3$, it is preferred that the second electrochemical cell exhibits additive properties with respect to NO and $NO_2$.

The inventors have discovered that two electrochemical cells, one having an additive response to two or more target gas species, and one having a selective response to at least one of the target gas species, can be provided by tailoring the current collectors of the two cells in order to provide additive and selective sensor responses (e.g., to enable dual $NO_X/NH_3$ detection and quantification). Signal strength and, in some instances, selectivity, is also enhanced by the SAL. These discoveries were achieved by making devices where the current collector completely covers the surface of the active electrode (>about 90% coverage) and utilizing a device architecture where both the counter and active electrodes are deposited on the same surface of the electrolyte, in spaced-apart relationship. As demonstrated by testing reported further herein, the inventors have discovered that electrochemical sensing reactions become controlled by the current collector in this alternative arrangement. For example, in electrochemical cells having the same active electrodes (based on $MgWO_4$ or $BaWO_4$), additive sensor responses are achieved in cells incorporating a platinum based current collector over the active electrode and selective responses are achieved in cells incorporating a gold based current collector over the active electrode. This is made clearer by the Examples described further herein.

Figure 21:
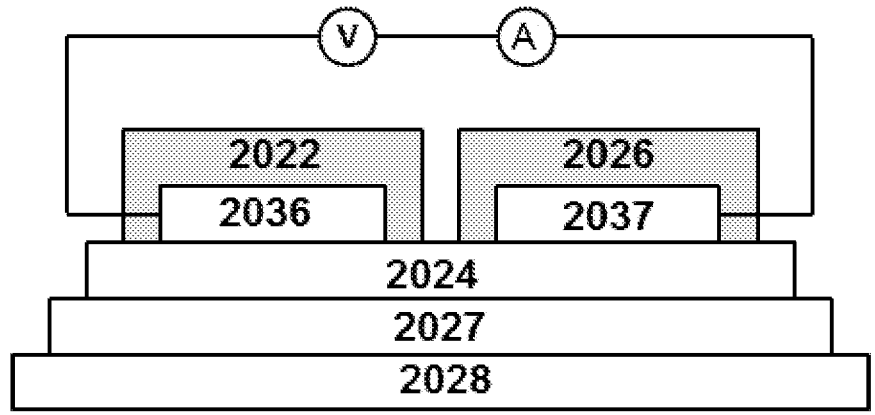
FIGS. 21-25 depict schematic cross-sectional views of alternative embodiments of sense elements wherein one or both of the electrodes comprise a current collecting layer located on the electrolyte layer and a catalyst layer is located over the current collecting layer, as further described herein.
Figure 22:
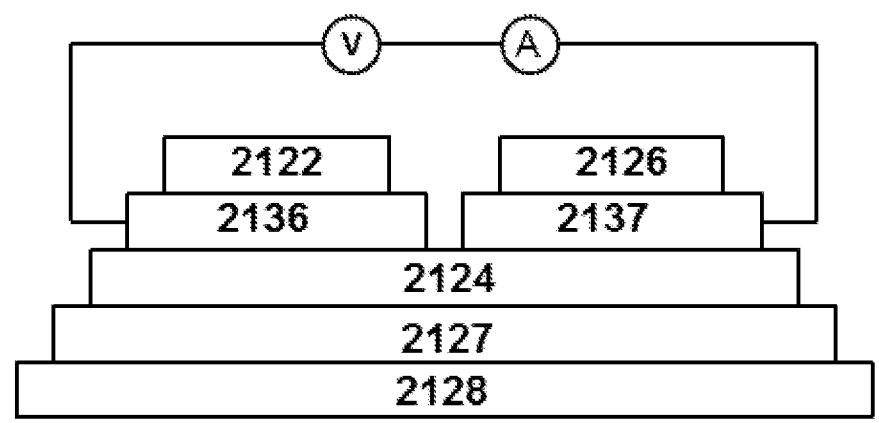
Figure 23:
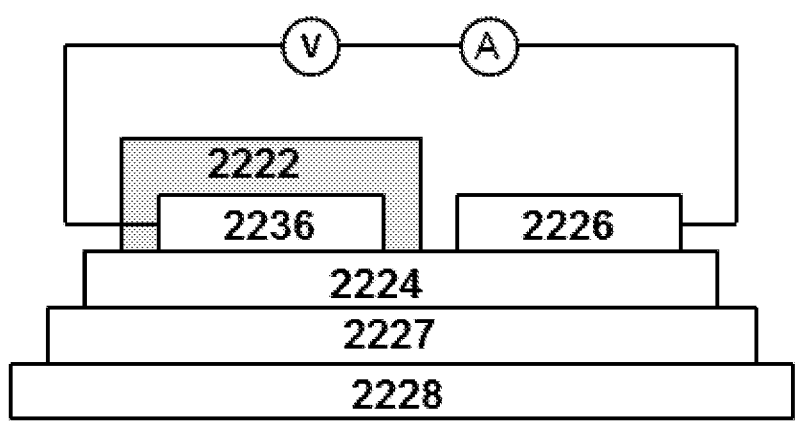

FIGS. 21-24 depict further alternative embodiments of sense elements of the present disclosure wherein one or both of the electrodes comprise a current collecting layer located on the electrolyte layer and a catalyst layer is located over the current collecting layer either covering at least about 90% of the top surface of the current collecting layer (FIGS. 22 and 24), or fully encapsulating the current collector layer between the catalyst layer and the electrolyte layer (FIGS. 21 and 23). A SAL is also provided in the embodiments of FIGS. 21-25, as shown.

In the embodiments of FIGS. 21-24, the current collector layers have higher electrical conductivity than the catalyst layers. The catalyst layers can be any of the materials previously identified herein for use as an active electrode layer, particular the compositions comprising a molybdate or tungstate (e.g., a molybdate or tungstate compound in combination with an electrolyte material and a metal, as described above). The current collector layer can be any of the materials previously identified herein for use as a current collector layer, particular a metal (e.g., Pt or Au) or a cermet of an electrolyte and a metal (e.g., Au/GDC, Pt/GDC, or Pt/ScSZ). Although the biasing voltage is applied between the current collector layers, and the resulting signal also obtained from between the current collector layers, as shown, it is believed that the catalyst layers will manipulate the concentrations of NO, $NO_2$ and $NH_3$ that are present at the catalyst/current collector interface, thereby changing the amount of current when a bias is applied (compared to the amount of current if no catalyst layer was present).

In FIG. 21, the sense element comprises an insulating substrate (2028), a conductive signal amplifying layer (2027), a ceramic electrolyte layer (2024) that can be porous or dense, a first current collector layer (2036) located on a portion of the upper surface of the electrolyte layer (2024), and a second current collector layer (2037) located on another portion of the upper surface of the electrolyte layer (2024) adjacent the first current collector layer (2036). A first catalyst layer (2022) encapsulates the first current collector layer (2036) (i.e., between the catalyst and the electrolyte), and a second catalyst layer (2026) encapsulates the second current collector layer (2037). The two current collector layers (2036, 2037) can be the same or different compositions, and the two catalyst layers (2022, 2026) can be the same or different compositions. However, at least one of either the current collector layers or the catalyst layers should have a different composition than the other current collector layer or catalyst layers (i.e., 2036 has a different composition than 2037, and/or 2022 has a different composition than 2026). It will also be understood that the SAL (2027) can optionally be fully encapsulated rather than partially encapsulated as shown (also the case with the sense elements of FIGS. 22-24).

The sense element of FIG. 22 is similar to that of FIG. 21, however, in this embodiment the catalyst layers (2122, 2126) do not fully encapsulate the underlying current collector layers (2136, 2137). The sense element of FIG. 22 also once again comprises an insulating substrate (2128), a conductive signal amplifying layer (2127), and a ceramic electrolyte layer (2124) that can be porous or dense. Once again the two current collector layers (2136, 2137) can be the same or different compositions, and the two catalyst layers (2122, 2126) can be the same or different compositions. However, at least one of either the current collector layers or the catalyst layers should have a different composition than the other current collector layer or catalyst layers (i.e., 2136 has a different composition than 2137, and/or 2122 has a different composition than 2126).

In the embodiment of FIG. 23, the sense element comprises an insulating substrate (2228), a conductive signal amplifying layer (2227), a ceramic electrolyte layer (2224) that can be porous or dense, a current collector layer (2236)

located on a portion of the upper surface of the electrolyte layer (2224), a counter electrode layer (2226) located on another portion of the upper surface of the electrolyte layer (2224) adjacent the current collector layer (2236). A catalyst layer (2222) encapsulates the current collector layer (2236) (i.e., between the catalyst and the electrolyte). The counter electrode layer 2226 can comprise any of the compositions described herein for use as a counter electrode or as a current collector.

Figure 24:
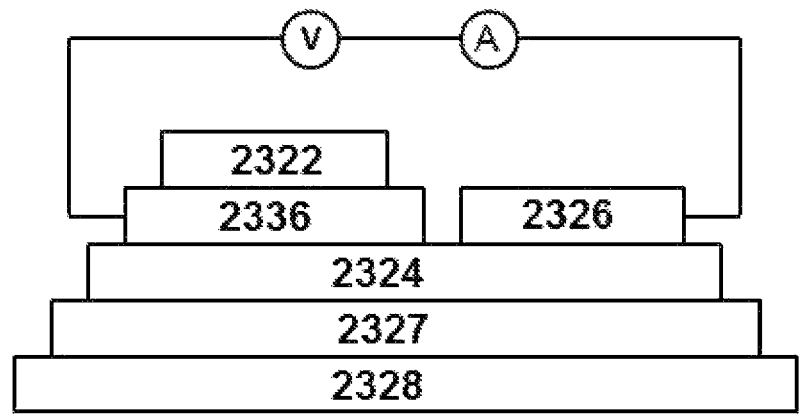

The sense element of FIG. 24 is similar to that of FIG. 23, however, in this embodiment the catalyst layer (2322) does not fully encapsulate the underlying current collector layer (2336). The sense element of FIG. 24 also once again comprises an insulating substrate (2328), a conductive signal amplifying layer (2327), a ceramic electrolyte layer (2324) that can be porous or dense, and a counter electrode layer (2326).

Figure 25:
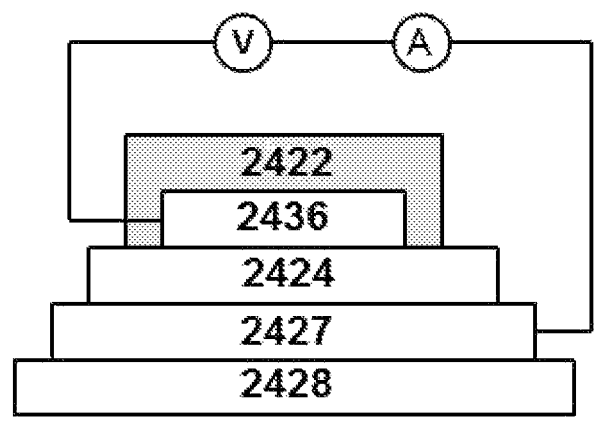

Finally, the sense element of FIG. 25 includes a catalyst layer (2422) that encapsulates a current collector layer (2436) (i.e., between the catalyst and the electrolyte (2424)). In this embodiment, however, the second (counter) electrode (2426) is buried under the electrolyte layer (2424) such that the counter electrode (2426) is located between the electrolyte layer (2424) and the substrate (2422). Thus, the sense element of FIG. 25 does not include a SAL.

EXAMPLES

Examples 1 and 2

Figure 13:
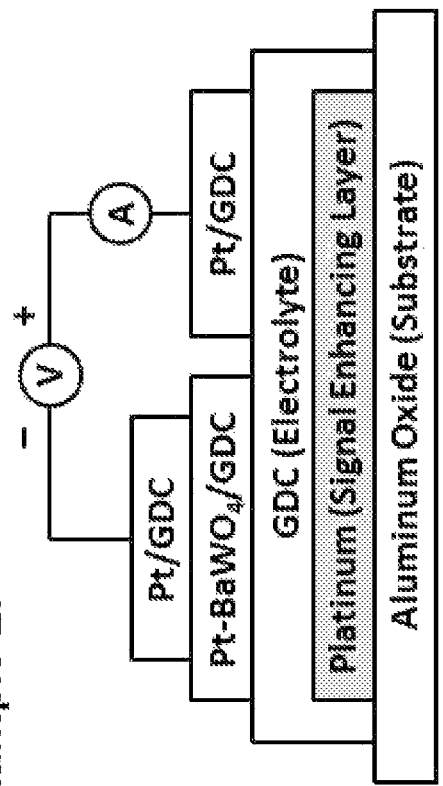
FIGS. 12 and 13 depict the sense elements used in Examples 1 and 2, as well as the results of the testing of these sensors with simulated combustion exhaust.
Figure 12:
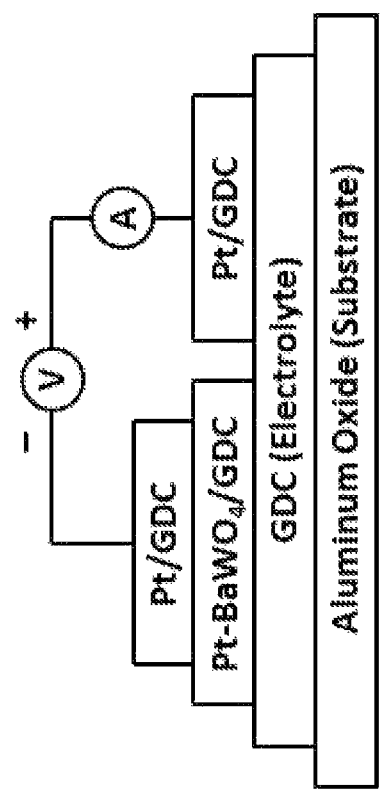

The effect of a signal amplifying layer on sensor performance was established using sensors that were identical in construction apart from one of them including a SAL encapsulated between the electrolyte layer and the substrate. As depicted in FIGS. 12 and 13, two sensors were constructed similar to that shown in FIG. 1. Thus, both sensors included an $Al_2O_3$ substrate, identical Pt—$BaWO_4$/GDC active electrode layers and Pt/GDC current collector and counter electrode layers. Identical processing methods were used in preparing and depositing these layers. The sensor of Example 1 was made without a platinum signal amplifying layer, while the sensor of Example 2 included a platinum signal amplifying layer between the GDC electrolyte layer and the substrate with the SAL fully encapsulated (as seen in FIG. 13). It should be noted that the dimensions of the sensor architectures shown in FIGS. 12 and 13 are not to scale. The gap between the active and counter electrodes on the electrolyte surface was approximately 500 microns, whereas the thickness of the GDC electrolyte layer (and thus the gap between the active electrode and the buried platinum layer) was approximately 30 microns.

The sensors of Examples 1 and 2 were exposed to a baseline simulated diesel exhaust gas atmosphere of 77 vol % $N_2$, 10 vol % $O_2$, 8 vol % $CO_2$, 5 vol % $H_2O$ and 1 ppm $SO_2$, with the sensor maintained at a temperature of 525° C. With a forward (positive) bias of 200 mV applied from the Pt/GDC current collector to the Pt/GDC counter electrode layers, the resulting currents were determined by measuring the voltage across a 100-ohm shunt resistor. The baseline signal (exposed only to the baseline simulated diesel exhaust gas) was measured, as well as signals (i.e., current) when 100 ppm of NO, $NO_2$ and $NH_3$ were added to the simulated exhaust gas. The sensitivities to 100 ppm exposures of NO, $NO_2$ and $NH_3$ were determined as the percent change in current signal when the analytes were present. The results of these tests are shown in FIGS. 12 and 13, wherein it is seen that the platinum signal amplifying layer increased the baseline signal from 0.28 to 3.8 µA (a more than tenfold increase). In addition, the sensitivities to each of the gas species tested was also significantly increased, thereby providing a significantly more useful sensor. The SAL provided a lateral current path and effectively increased the areas of the active and counter electrodes. Thus, one can visualize that the lateral current path provided by the platinum is a faster path for charge carriers, even though two additional electrochemical reactions must occur (conversion of oxygen ions to electrons at the GDC/Pt-SAL interface and conversion of electrons back to oxygen ions at the Pt-SAL/GDC interface).

Examples 3-10

The ability to tailor the response characteristics of the sensor by varying the compositions of the electrode and current collector layers was demonstrated by fabricating various sensors and determining their performance in simulated diesel exhaust (baseline) as well as simulated exhaust with 100 ppm of NO, $NO_2$ or $NH_3$. The sensors of Examples 3-10 were fabricated as described above for Example 2 (i.e., the architecture of FIG. 1, including a fully encapsulated Pt SAL). Thus, the common electrolyte layer (24) was GDC, and the active electrode (22), current collector (36) and counter-electrode (26) layers were varied, as reported in Table 1 below. The sensors were tested with forward (positive) bias applied from the current collector (36) to the counter electrode (26) layers. The sensors were tested, as described above for Examples 1 and 2, with bias voltage of 200 mV at a temperature of 525° C. The baseline gas atmosphere consisted of 8 vol % $CO_2$, 5% vol % $H_2O$, 1 ppm $SO_2$, 10 vol % $O_2$, and 77 vol % $N_2$, and sensor responses were measured for exposures to the baseline atmosphere with analytes of 100 ppm NO, 100 ppm $NO_2$, or 100 ppm $NH_3$ added thereto. Results are summarized in Table 2 and described in the paragraphs that follow.

TABLE 1

Compositions of component layers in surface-electrode sensor Examples 3-10.

| Example | Active Electrode | Current Collector | Counter Electrode |
|---|---|---|---|
| 3 | Pt—$MgWO_4$/GDC | Au/GDC | Pt/ScSZ |
| 4 | Pt—$MgWO_4$/GDC | Pt/ScSZ | Pt/ScSZ |
| 5 | Pt—$BaWO_4$/GDC | Au/GDC | Pt/ScSZ |
| 6 | Pt—$BaWO_4$/GDC | Pt/ScSZ | Pt/ScSZ |
| 7 | $MgWO_4$/GDC | Pt/ScSZ | Pt/ScSZ |
| 8 | Pt—$MgWO_4$/GDC | Pt | Pt |
| 9 | Pt—$MgWO_4$/GDC | Au/GDC | Au/GDC |
| 10 | Pt—$MgWO_4$/GDC | Pt/ScSZ | Au/GDC |

TABLE 2

Sensing data for surface-electrode sensor Examples 3-10.

| Example | Bias (mV) | Baseline Current Signal (µA) | Sensitivity to 100 ppm NO | Sensitivity to 100 ppm $NO_2$ | Sensitivity to 100 ppm $NH_3$ |
|---|---|---|---|---|---|
| 3 | 200 | 8.90 | 33% | 43% | 2.5% |
| 4 | 200 | 6.53 | 39% | 31% | 33% |
| 5 | 200 | 5.41 | 91% | 108% | 49% |
| 6 | 200 | 3.81 | 167% | 160% | 164% |

TABLE 2-continued

Sensing data for surface-electrode sensor Examples 3-10.

| Example | Bias (mV) | Baseline Current Signal (μA) | Sensitivity to 100 ppm NO | Sensitivity to 100 ppm $NO_2$ | Sensitivity to 100 ppm $NH_3$ |
|---|---|---|---|---|---|
| 7 | 200 | 0.85 | 21% | 13% | 21% |
| 8 | 200 | 0.140 | 5.7% | 7.1% | 1.4% |
| 9 | 200 | 9.44 | 23% | 45% | 30% |
| 10 | 200 | 4.72 | 95% | 108% | 181% |

Figure 14:
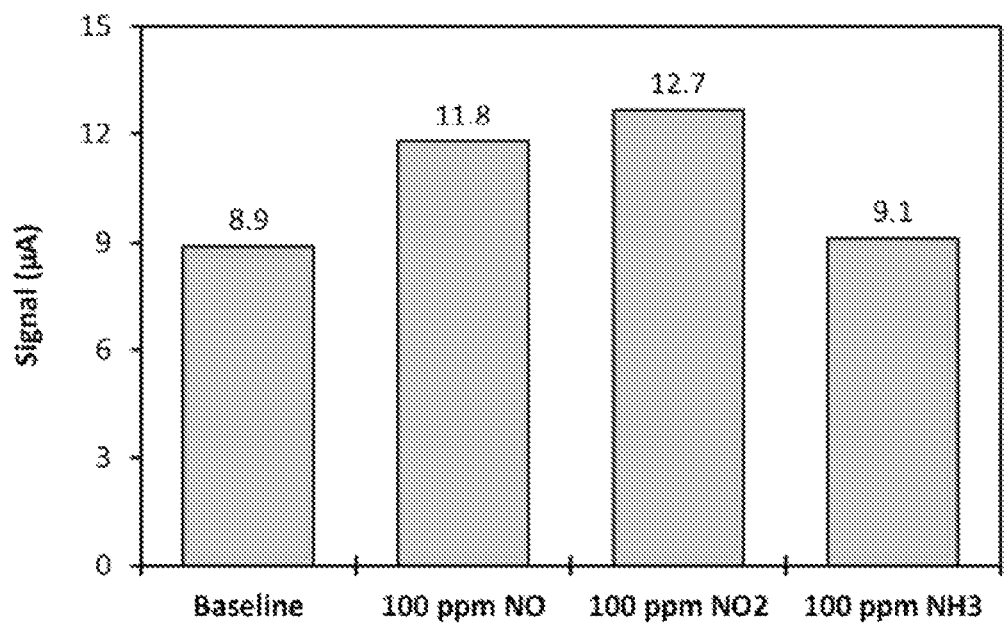
FIG. 14 is a bar chart comparing current signals in simulated combustion exhaust atmospheres (baseline gas, baseline with 100 ppm NO, baseline with 100 ppm $NO_2$, and baseline with 100 ppm $NH_3$) for the sensor of Example 3, tested at 525° C. with an applied bias voltage of 200 mV.

Test data obtained for the sensor of Example 3, with a Pt—$MgWO_4$/GDC active electrode, an Au/GDC current collector and a Pt/ScSZ counter electrode, are presented in Table 2 and FIG. 14. With a 200 mV bias applied at a temperature of 525° C., this sensor exhibited a baseline current signal of 8.9 μA, with selective sensing behavior to NO and $NO_2$ (33% and 43% sensitivities to 100 ppm NO and 100 ppm $NO_2$, respectively, and only 2% sensitivity to 100 ppm $NH_3$). The lack of sensitivity to $NH_3$ is seen in FIG. 14 wherein the signal when 100 ppm $NH_3$ is added to the baseline simulated diesel exhaust is only slightly higher than the baseline signal (9.1 μA vs. 8.9 μA).

Figure 15:
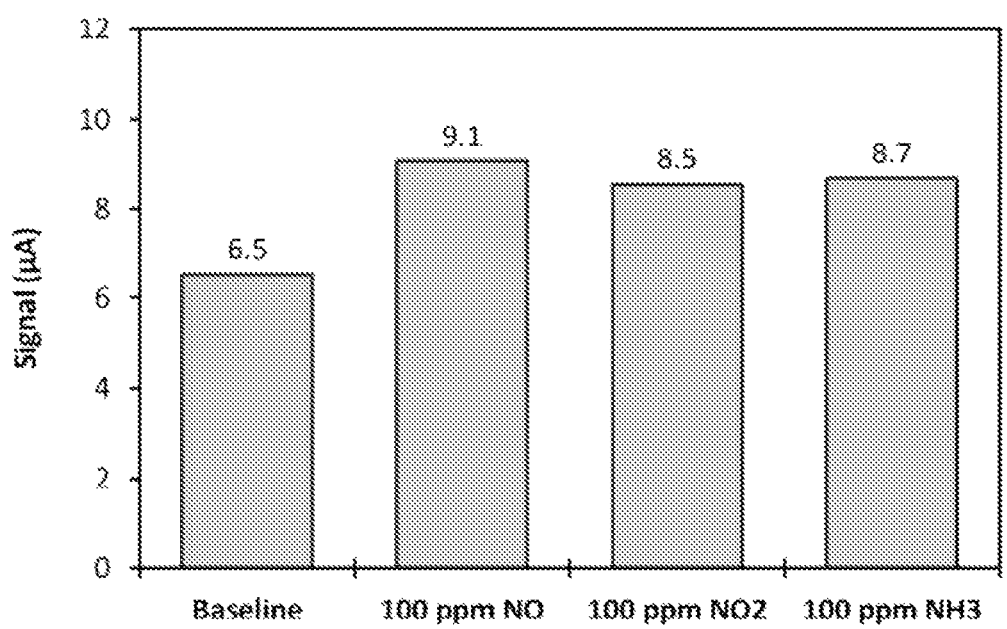
FIG. 15 is a bar chart comparing current signals in simulated combustion exhaust atmospheres (baseline gas, baseline with 100 ppm NO, baseline with 100 ppm $NO_2$, and baseline with 100 ppm $NH_3$) for the sensor of Example 4, tested at 525° C. with an applied bias voltage of 200 mV.

Test data obtained for the sensor of Example 4, with a Pt—$MgWO_4$/GDC active electrode, a Pt/SCSZ current collector and a Pt/ScSZ counter electrode, are presented in Table 2 and FIG. 15. With a 200 mV bias applied at a temperature of 525° C., this sensor exhibited a baseline current signal of 6.5 μA, with additive sensing behavior to NO, $NO_2$ and $NH_3$ (39%, 31% and 33% percent sensitivities to 100 ppm NO, 100 ppm $NO_2$ and 100 ppm $NH_3$, respectively).

Figure 16:
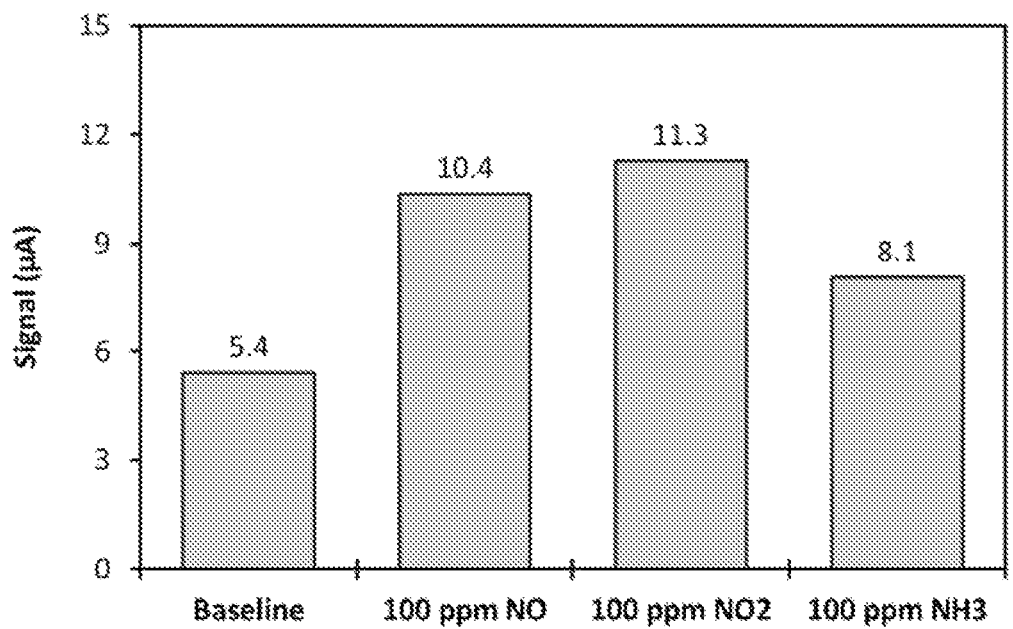
FIG. 16 is a bar chart comparing current signals in simulated combustion exhaust atmospheres (baseline gas, baseline with 100 ppm NO, baseline with 100 ppm $NO_2$, and baseline with 100 ppm $NH_3$) for the sensor of Example 5, tested at 525° C. with an applied bias voltage of 200 mV.

Test data obtained for the sensor of Example 5, with a Pt—$BaWO_4$/GDC active electrode, an Au/GDC current collector and Pt/ScSZ counter electrode, are presented in Table 2 and FIG. 16. With a 200 mV bias applied at a temperature of 525° C., this sensor exhibited a baseline current signal of 5.4 μA, with nominally selective sensing behavior to NO and NO2 (91% and 108% percent sensitivities, respectively, compared to 49% sensitivity to $NH_3$). Thus, the replacement of $MgWO_4$ with $BaWO_4$ in the active electrode of this sensor led to a substantial increase in $NO_X$ sensitivity, although a significant $NH_3$ response also was observed. In order to improve the usefulness of this sensor for selective $NO_X$ detection, the $NH_3$ response would need to be reduced, such as by modifying thicknesses and/or porosities of the active electrode and current collector layers, or by changing the composition of the current collector layer.

Figure 17:
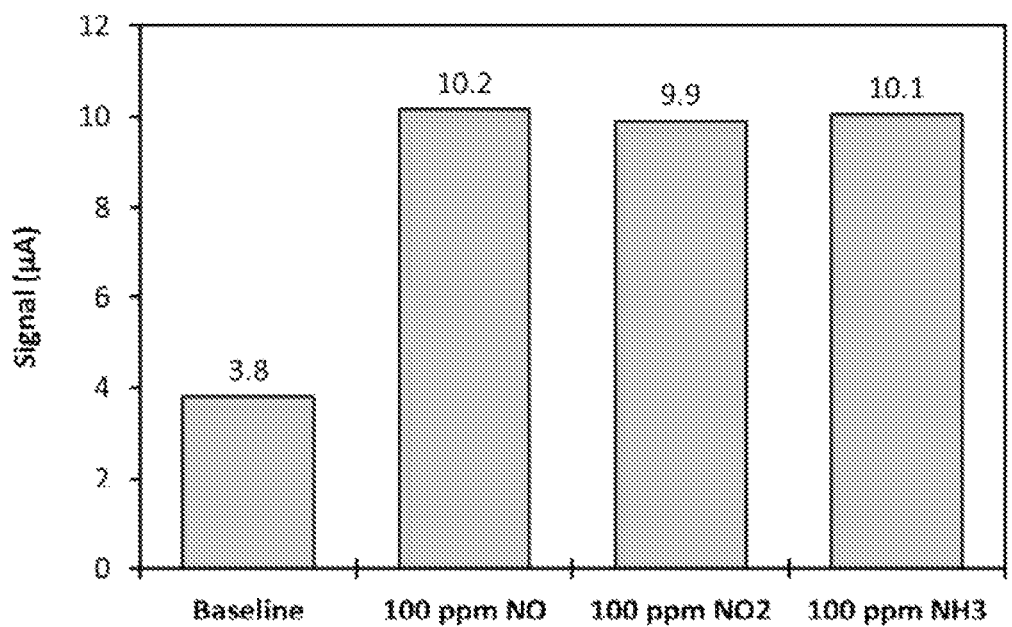
FIG. 17 is a bar chart comparing current signals in simulated combustion exhaust atmospheres (baseline gas, baseline with 100 ppm NO, baseline with 100 ppm $NO_2$, and baseline with 100 ppm $NH_3$) for the sensor of Example 6, tested at 525° C. with an applied bias voltage of 200 mV.

Test data obtained for the sensor of Example 6, with a Pt—$BaWO_4$/GDC active electrode, a Pt/SCSZ current collector and a Pt/ScSZ counter electrode are presented in Table 2 and FIG. 17. With a 200 mV bias applied at a temperature of 525° C., this sensor exhibited a baseline current signal of 3.8 μA, with additive sensing behavior to NO, $NO_2$ and $NH_3$ (167%, 164% and 164% sensitivities to 100 ppm NO, 100 ppm $NO_2$ and 100 ppm $NH_3$, respectively). Thus, the replacement of $MgWO_4$ with $BaWO_4$ in the active electrode of this additive sensor led to a four-fold increase in $NO_X$ and $NH_3$ sensitivities.

Test data obtained for the sensor of Example 7, with a $MgWO_4$/GDC active electrode (without platinum in the active electrode), a Pt/SCSZ current collector and a Pt/ScSZ counter electrode, are presented in Table 2. With a 200 mV bias applied at a temperature of 525° C., this sensor exhibited a very low baseline current signal of 0.85 μA, with relatively low and less than optimal additive sensitivities (21%, 13% and 21% sensitivities to 100 ppm NO, 100 ppm $NO_2$ and 100 ppm $NH_3$, respectively). The data demonstrate the advantage of including platinum (or another metal) in the active electrode in order to achieve more desirable $NO_X$ and $NH_3$ sensing behavior.

Test data obtained for the sensor of Example 8, with a Pt—$MgWO_4$/GDC active electrode, a platinum current collector and a platinum counter electrode (without ScSZ or GDC in the current collector or counter electrodes), are presented in Table 2. With a 200 mV bias applied at a temperature of 525° C., this sensor exhibited a significantly reduced baseline current signal of 0.14 μA, with very low sensitivities of 6%, 7% and 1% to 100 ppm NO, 100 ppm $NO_2$ and 100 ppm $NH_3$, respectively. The data demonstrate the advantage of including electrolyte material (e.g., ScSZ or GDC) in the current collector and counter electrode layers (at least for this particular sensor configuration and active electrode material).

Test data obtained for the sensor of Example 9, with a Pt—$MgWO_4$/GDC active electrode, an Au/GDC current collector and an Au/GDC counter electrode, are presented in Table 2. With a 200 mV bias applied at a temperature of 525° C., this sensor exhibited a relatively high baseline current signal of 9.4 μA, with 23%, 45% and 30% sensitivities to 100 ppm NO, 100 ppm $NO_2$ and 100 ppm $NH_3$, respectively. Thus, replacement of Pt/ScSZ with Au/GDC in the counter electrode resulted in reduction in selectivity as compared to Example 3, thus demonstrating the effect of changing the metal used in a cermet counter electrode for purposes of manipulating sensor response, as well as the advantage of using platinum rather than gold in the cermet counter electrode for this particular sensor configuration and active electrode material.

Test data obtained for the sensor of Example 10, with a Pt—$MgWO_4$/GDC active electrode, a Pt/ScSZ current collector and an Au/GDC counter electrode, are presented in Table 2. With a 200 mV bias applied at a temperature of 525° C., this sensor exhibited a baseline current signal of 4.7 μA, with 95%, 108% and 181% percent sensitivities to 100 ppm NO, 100 ppm $NO_2$ and 100 ppm $NH_3$, respectively. Thus, replacement of Pt/ScSZ with Au/GDC in the counter electrode resulted in a loss of additive behavior, again confirming that platinum (and not gold) is preferred to be present in the cermet counter electrode for this particular sensor configuration and active electrode material.

Examples 11 and 12

Figure 18:
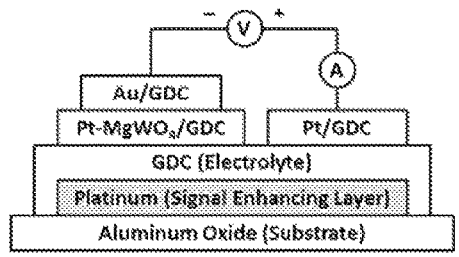
FIG. 18 schematically depicts the sense element used in Example 11, operated with a forward bias and depicting the results of the testing of this sensor with simulated combustion exhaust and showing the response to NO, $NO_2$ and $NH_3$ at varying oxygen levels in the gas sample.
Figure 18:
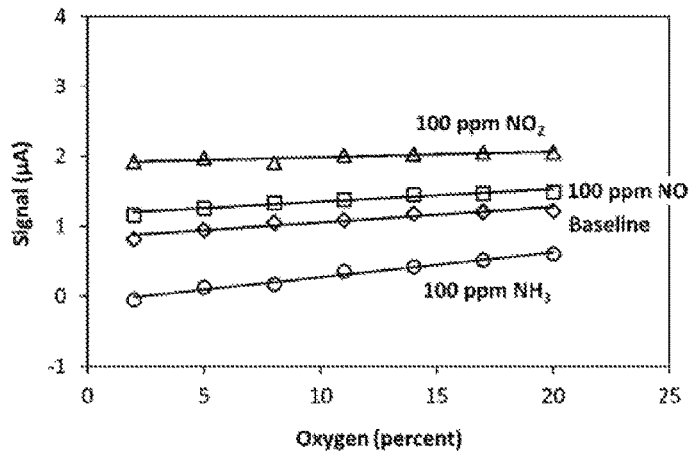
Figure 19:
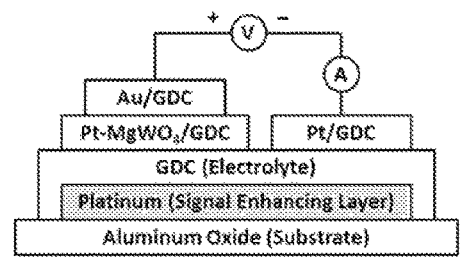
FIG. 19 schematically depicts the sense element used in Example 12, operated with a reverse bias and depicting the results of the testing of this sensor with simulated combustion exhaust and showing the response to NO, $NO_2$ and $NH_3$ at varying oxygen levels in the gas sample.
Figure 19:
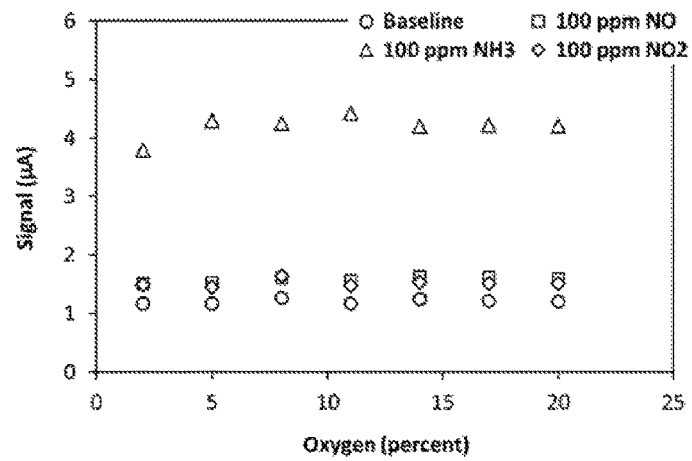

The demonstration of how the sensors described herein can be adapted for ammonia detection is illustrated in Examples 11 and 12. A sensor was fabricated as described above for Example 2 (i.e., the architecture of FIG. 1, including a fully encapsulated Pt SAL). The sensor employed an $Al_2O_3$ substrate, a Pt—$MgWO_4$/GDC active electrode layer, a Au/GDC current collector layer and a Pt/GDC counter electrode layer, as shown in FIGS. 18 and 19. Also, compared to the previous Examples, the Pt—$MgWO_4$/GDC, Pt/GDC and Au/GDC layers were made with higher surface area constituents and with higher annealing temperatures, which led to increased density (and durability) of these layers.

The sensors were tested at 525° C. in a baseline gas atmosphere consisted of 8 vol % $CO_2$, 5% vol % $H_2O$, 1 ppm $SO_2$, 2-20 vol % $O_2$, and 67-85 vol % $N_2$, sensor responses were also observed for exposures to analytes of 100 ppm NO, 100 ppm $NO_2$, or 100 ppm $NH_3$, with bias voltages ranging from −200 to +200 mV. Data obtained with a forward bias of 200 mV are shown in FIG. 18. When tested in the forward bias mode (i.e., with oxygen ions being generated at the active electrode and conducting through the electrolyte to the counter electrode), the sensor was highly cross-sensitive to oxygen, the responses to NO and $NO_2$ were positive and unequal (33% and 108% percent, respectively), and the response to $NH_3$ was highly negative (−86%), with an oxygen content of 5 vol %.

Data obtained with reverse bias of −200 mV are provided in FIG. 19. When tested in the reverse bias mode (i.e., with oxygen ions being generated at the counter electrode and conducting through the electrolyte to the active electrode), the sensor was slightly cross-sensitive to oxygen, NO and $NO_2$ responses were slightly positive (31% and 25%, respectively), and the $NH_3$ response was also highly positive (267%).

Figure 20:
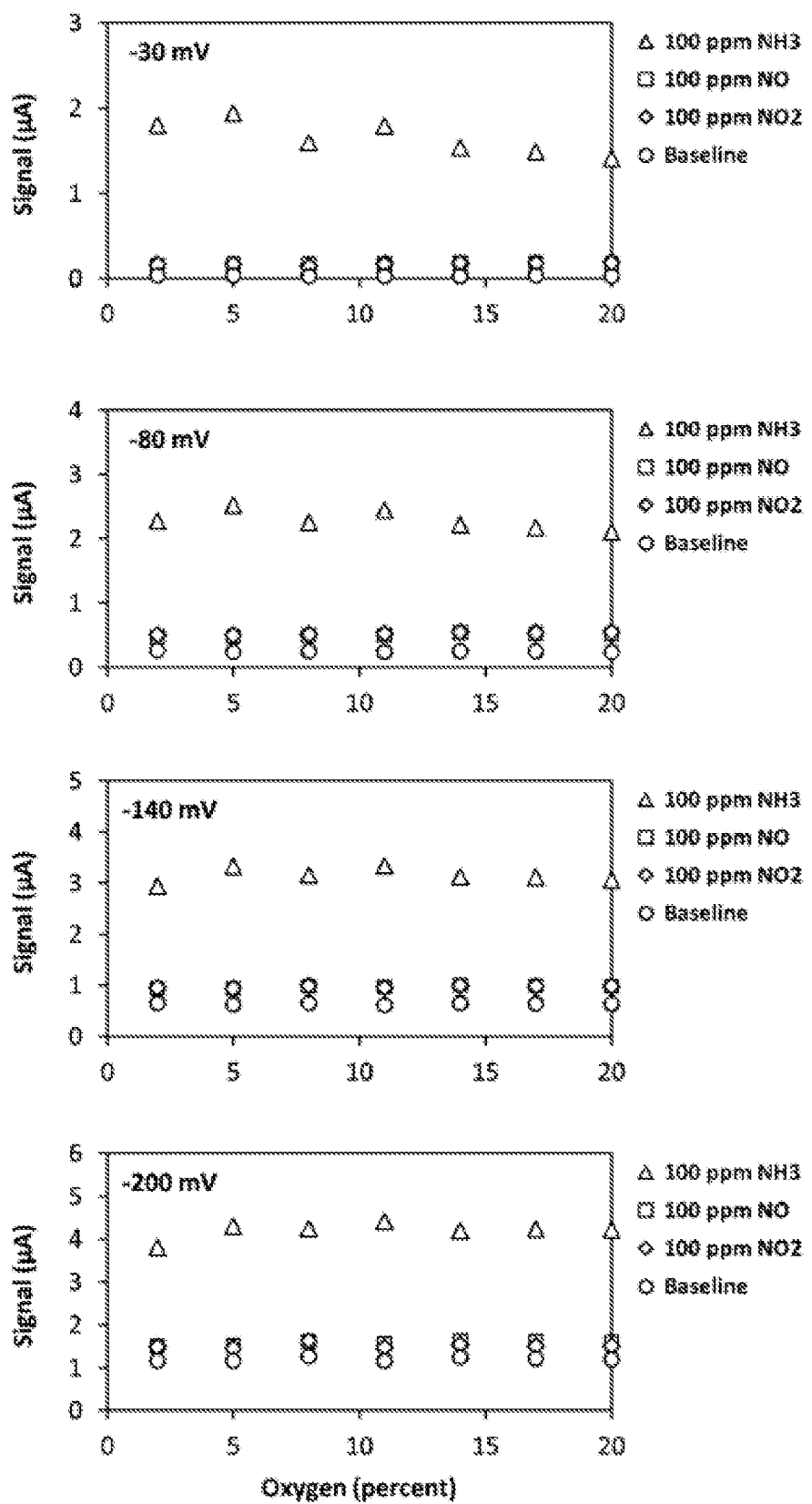
FIG. 20 graphically depicts the results of the testing of the sense element of FIG. 19, showing the response to NO, $NO_2$ and $NH_3$ at varying oxygen levels in the gas sample and at varying levels of reverse bias applied to the electrochemical cell.

The impact of oxygen content on $NO_X$ and $NH_3$ responses at different reverse bias voltages (at 525° C.) is shown in FIG. 20. At lower bias voltages (−30 and −80 mV), the $NH_3$ responses were slightly cross-sensitive to oxygen, with signal strength being lower at higher oxygen contents. At higher bias voltages (−140 and −200 mV), however, the $NH_3$ sensitivities were insensitive to oxygen content. The combination of very high sensitivity to $NH_3$ (relative to $NO_X$) and insensitivity to oxygen is advantageous for use as a stand-alone $NH_3$ sensor or as an $NH_3$ selective cell in a dual $NO_X$/$NH_3$ sensor.

While various embodiments of sensors, as well as methods of fabrication and use of sensors, have been described in detail above, it will be understood that the components, features and configurations, as well as the methods of manufacturing the devices and methods described herein are not limited to the specific embodiments described herein. For example, components, features, configurations, and methods of fabrication or use described in the context of one embodiment above may be incorporated into any of the other embodiments. Furthermore, not limited to the further description provided below, additional and alternative suitable components, features, configurations, and methods of using the devices, as well as various ways in which the teachings herein may be combined and interchanged, will be apparent to those of ordinary skill in the art in view of the teachings herein.

Having shown and described various embodiments in the present disclosure, further modifications and adaptations of the methods, systems and devices described herein may be accomplished by one of ordinary skill in the art without departing from the scope of the present disclosure. Several of such potential modifications have been mentioned, and others will be apparent to those skilled in the art. Accordingly, the scope of the present invention should be considered in terms of the following claims and is understood not to be limited to the details of structure and operation shown and described in the specification and drawings.

What is claimed is:

1. An amperometric electrochemical sensor for measuring a concentration of one or more target gas species in a gas sample or gas stream, the sensor comprising a first electrochemical cell having first and second surface electrodes, an electrolyte layer, a conductive, passive signal amplifying layer ("SAL"), and an electrical heater, wherein the heater is electrically isolated from the electrolyte layer, and further wherein at least a portion of the electrolyte layer is located between the surface electrodes and the SAL such that the SAL is in direct, electrically conductive contact with the electrolyte layer but is not in direct contact with the surface electrodes.

2. The sensor of claim 1, wherein said first surface electrode comprises at least one molybdate or tungstate compound, and further wherein said at least one molybdate or tungstate compound comprises $A_X(Mo_{(1-Z)}W_Z)_YO_{(X+3Y)}$, wherein X and Y are each independently selected integers from 1 to 5, $0 \leq Z \leq 1$, and A is one or more of Mg, Zn, Ni, Co, Fe, Mn, Cu, Ca, Sr, Ba, and Pb.

3. The sensor of claim 2, wherein said at least one molybdate or tungstate compound comprises $MgMoO_4$, $MgWO_4$, $BaWO_4$ or $CoWO_4$.

4. The sensor of claim 2, wherein said first surface electrode comprises a composite mixture of: (a) said at least one molybdate or tungstate compound; and (b) at least one ceramic electrolyte material.

5. The sensor of claim 4, wherein said first surface electrode further comprises about 0.1% to 10% by weight of at least one metal chosen from the group consisting of: Pt, Pd, Rh, Ru, Ir, alloys of any of the foregoing, and a mixture of two or more of the foregoing.

6. The sensor of claim 4, wherein said at least one ceramic electrolyte material of the first surface electrode is selected from the group consisting of:
(a) cerium oxide doped with one or more of Ca, Sr, Sc, Y, Pr, Nd, Pm, Sm, Eu, Gd, Tb, Dy, Ho, Er, Tm, Yb, or La;
(b) zirconium oxide doped with one or more of Ca, Mg, Sc, Y, or Ce; and
(c) lanthanum gallium oxide doped with one or more of Sr, Mg, Zn, Co, or Fe.

7. The sensor of claim 2, wherein said second surface electrode comprises a cermet of: (a) platinum or gold; and (b) gadolinium-doped ceria ("GDC"), samarium-doped ceria ("SDC"), zirconium-doped ceria ("ZDC"), yttrium stabilized zirconia ("YSZ"), or scandium stabilized zirconia ("ScSZ").

8. The sensor of claim 2, wherein said second surface electrode comprises a composite mixture of: (a) at least one molybdate or tungstate compound; (b) at least one ceramic electrolyte material; (c) and at least one metal chosen from the group consisting of: Pt, Pd, Rh, Ru, Ir, alloys of any of the foregoing, and a mixture of two or more of the foregoing.

9. The sensor of claim 2, further comprising a current collecting layer on at least one of said first and second surface electrodes, wherein said current collecting layer comprises:
a noble metal chosen from the group consisting of platinum, palladium, gold, silver, or an alloy of two or more of the foregoing noble metals;
an alloy of platinum, palladium, gold or silver and one or more base metals; or
a cermet of platinum, palladium, gold or silver and a ceramic electrolyte material.

10. The sensor of claim 9, wherein said current collecting layer is provided on said first surface electrode and comprises a cermet of: (a) platinum or gold; and (b) GDC, SDC, ZDC, YSZ or ScSZ.

11. The sensor of claim 1, wherein said first surface electrode comprises a composite mixture of:
(a) a tungstate compound comprising $MgWO_4$, $BaWO_4$ or $CoWO_4$;
(b) an electrolyte chosen from the group consisting of gadolinium-doped ceria ("GDC") and samarium-doped ceria ("SDC"); and
(c) about 1% to 5% by weight of Pt, Pd, Rh, Ru, Ir, or alloys or mixtures of any of the foregoing metals;

wherein the volumetric ratio of the electrolyte to the tungstate compound is between about 2.5:7.5 and 7.5:2.5.

12. The sensor of claim 1, wherein said first surface electrode comprises a ceramic phase and a metallic phase, and further wherein the ceramic phase of the first surface electrode comprises a zirconia-based electrolyte material, a ceria-based electrolyte material, a bismuth oxide based electrolyte material, a lanthanum gallium oxide based electrolyte material, aluminum oxide or magnesium oxide, or a mixture thereof, and the metallic phase comprises Ag, Pt, Pd, Rh, Ru, Ir, or an alloy or mixture thereof.

13. The sensor of claim 1, wherein said second surface electrode is chosen from the group consisting of:
a metal chosen from the group consisting of Ag, Au, Pt, Pd, Rh, Ru, Ir, and alloys or mixtures of the foregoing;
a conductive perovskite; and
a cermet of a metal and a ceramic.

14. The sensor of claim 1, wherein at least one of said first and second surface electrodes comprises a current collecting layer positioned on the electrolyte layer, and a catalyst layer located over the current collecting layer.

15. The sensor of claim 14, wherein said catalyst layer comprises a composite mixture of: (a) at least one molybdate or tungstate compound; and (b) at least one ceramic electrolyte material; and
further wherein said current collecting layer comprises:
a noble metal chosen from the group consisting of platinum, palladium, gold, silver, or an alloy of two or more of the foregoing noble metals;
an alloy of platinum, palladium, gold or silver and one or more base metals; or
a cermet of platinum, palladium, gold or silver and a ceramic electrolyte material.

16. The sensor of claim 1, further comprising a substrate on which said respective first and second surface electrodes, electrolyte layer and SAL are supported, wherein said SAL is located between the electrolyte layer and the substrate, the substrate chosen from the group consisting of: an insulating ceramic, a metal coated with an insulating material, and a cermet coated with an insulating material.

17. The sensor of claim 16, wherein the electrical heater is located between the SAL and the substrate.

18. The sensor of claim 1, further comprising a substrate on which said respective first and second surface electrodes, said electrolyte layer and said SAL are supported, wherein said SAL is encapsulated between the electrolyte layer and the substrate.

19. The sensor of claim 1 wherein said SAL comprises a material chosen from the group consisting of: Pt, Pd, Au, Ag, and alloys of two or more of the foregoing metals; a conductive ceramic; and a conductive cermet.

20. The sensor of claim 19, wherein said SAL consists essentially of platinum.

21. The sensor of claim 1, further comprising a second electrochemical cell comprising first and second surface electrodes on an electrolyte layer, wherein the sensor is adapted for measuring concentrations of two or more target gas species in the gas sample or the gas stream.

22. The sensor of claim 21, wherein the first electrochemical cell exhibits an additive response with respect to a first target gas species and a second target gas species of said two or more target gas species and the second electrochemical cell exhibits a selective response to the first target gas species in the presence of the second target gas species such that the sensor is capable of measuring the respective concentrations of said first and second target gas species, and further wherein:
said second electrochemical cell further comprises a passive signal amplifying layer ("SAL"), with at least a portion of the electrolyte layer of said second electrochemical cell located between the surface electrodes and the SAL of that cell, such that the SAL is in direct, electrically conductive contact with the electrolyte layer of said second electrochemical cell but is not in direct contact with the surface electrodes of said second electrochemical cell.

23. The sensor of claim 22, wherein said first and second electrochemical cells share at least one of a common electrolyte layer, a common second surface electrode and a common SAL.

24. A method of detecting the concentrations of NOx and/or NH$_3$ in a gas sample or stream, comprising the steps of:
(a) locating the sensor of claim 1 such that the electrochemical cell is exposed to the gas sample or stream;
(b) applying a bias to the first electrochemical cell;
(c) measuring the resulting currents between the surface electrodes; and
(d) determining the concentration of NOx and/or NH$_3$ based on the measured current(s).

* * * * *